United States Patent
Chen et al.

(10) Patent No.: US 7,115,391 B1
(45) Date of Patent: Oct. 3, 2006

(54) PRODUCTION OF RECOMBINANT AAV USING ADENOVIRUS COMPRISING AAV REP/CAP GENES

(75) Inventors: Haifeng Chen, Castro Valley, CA (US); Gary Kurtzman, Bryn Mawr, PA (US)

(73) Assignee: Genovo, Inc., Seattle, WA (US)

( * ) Notice: Subject to any disclaimer, the term of this patent is extended or adjusted under 35 U.S.C. 154(b) by 121 days.

(21) Appl. No.: 10/089,394

(22) PCT Filed: Sep. 29, 2000

(86) PCT No.: PCT/US00/26948

§ 371 (c)(1), (2), (4) Date: Mar. 29, 2002

(87) PCT Pub. No.: WO01/25462

PCT Pub. Date: Apr. 12, 2001

Related U.S. Application Data

(60) Provisional application No. 60/157,466, filed on Oct. 1, 1999.

(51) Int. Cl.
- C12P 21/06 (2006.01)
- C12N 15/63 (2006.01)
- C12N 15/64 (2006.01)
- A61K 39/12 (2006.01)
- A01N 63/00 (2006.01)

(52) U.S. Cl. ............ 435/69.1; 435/455; 435/456; 435/320.1; 435/91.41; 435/91.42; 424/93.2; 424/93.21; 424/199.1

(58) Field of Classification Search .......... 435/320.1, 435/69.1, 456, 235.1; 424/93.1, 93.2, 199.1
See application file for complete search history.

(56) References Cited

U.S. PATENT DOCUMENTS

| | | | |
|---|---|---|---|
| 5,354,678 A | | 10/1994 | Lebkowski et al. |
| 5,589,377 A | * | 12/1996 | Lebkowski et al. ........ 435/369 |
| 5,622,856 A | * | 4/1997 | Natsoulis ................. 435/325 |
| 5,658,776 A | | 8/1997 | Flotte et al. |
| 5,658,785 A | | 8/1997 | Johnson |
| 5,753,500 A | | 5/1998 | Shenk et al. |
| 5,780,280 A | | 7/1998 | Lebkowski et al. |
| 5,837,484 A | | 11/1998 | Trempe et al. |
| 5,856,152 A | | 1/1999 | Wilson et al. |
| 5,871,982 A | | 2/1999 | Wilson et al. |
| 6,001,650 A | | 12/1999 | Colosi |
| 6,037,177 A | * | 3/2000 | Snyder ................. 435/455 |
| 6,274,354 B1 | * | 8/2001 | Wilson et al. ........... 435/91.42 |
| 6,383,794 B1 | * | 5/2002 | Mountz et al. .......... 435/235.1 |
| 6,420,170 B1 | * | 7/2002 | Perricaudet et al. ...... 435/320.1 |
| 6,482,634 B1 | | 11/2002 | Wilson et al. |
| 6,491,907 B1 | * | 12/2002 | Rabinowitz et al. ....... 424/93.2 |
| 6,509,150 B1 | * | 1/2003 | Salvetti et al. .............. 435/5 |
| 6,521,426 B1 | * | 2/2003 | Ciliberto et al. .......... 435/70.1 |
| 6,541,258 B1 | | 4/2003 | Allen et al. |
| 6,548,286 B1 | | 4/2003 | Samulski et al. |
| 6,566,118 B1 | | 5/2003 | Atkinson et al. |
| 6,686,200 B1 | | 2/2004 | Dong et al. |
| 2003/0175974 A1 | | 9/2003 | Allen |

FOREIGN PATENT DOCUMENTS

| | | |
|---|---|---|
| EP | 1 007 637 B1 | 6/2000 |
| JP | WO 96/13598 A3 | 5/1996 |
| WO | WO 95/06743 * | 8/1994 |
| WO | WO 95/06743 A2 | 3/1995 |
| WO | WO 95/06743 A3 | 3/1995 |
| WO | WO 95/13365 | 5/1995 |
| WO | WO 95/13392 | 5/1995 |
| WO | WO 96/13598 A2 | 5/1996 |
| WO | WO 96/17947 | 6/1996 |
| WO | WO 97/00326 A1 | 1/1997 |
| WO | WO 97/06272 A2 | 2/1997 |
| WO | WO 97/06272 A3 | 2/1997 |
| WO | WO 97/06826 A1 | 2/1997 |
| WO | WO 97/49824 A1 | 12/1997 |
| WO | WO 98/06864 A2 | 2/1998 |
| WO | WO 98/06864 A3 | 2/1998 |
| WO | WO 98/10088 | 3/1998 |
| WO | WO 98/27204 A2 | 6/1998 |
| WO | WO 98/27204 A3 | 6/1998 |
| WO | WO 98/46728 A1 | 10/1998 |
| WO | WO 99/11764 | 3/1999 |
| WO | WO 99/14354 | 3/1999 |
| WO | WO 99/15685 A1 | 4/1999 |
| WO | WO 00/14205 | 3/2000 |

OTHER PUBLICATIONS

Jones, S. N. and Shenk, T. (Jan. 1978). "Isolation of Deletion and Substitution Mutants of Adenovirus Type 5," *Cell* 13(1):181-188.

(Continued)

*Primary Examiner*—Dave Trong Nguyen
*Assistant Examiner*—Maria Marvich
(74) *Attorney, Agent, or Firm*—Morrison & Foerster LLP

(57) ABSTRACT

This invention relates to novel adenoviruses useful in the production of high titers of recombinant adeno-associated virus (rAAV) comprising a foreign DNA insert and methods of making these adenoviruses. The adenovirus comprises the AAV rep gene in which the p5 promoter is replaced by a minimal promoter or by no promoter. The invention also provides methods of producing high levels of rAAV as a substantially homogenous preparation and composition of rAAV.

19 Claims, 10 Drawing Sheets

OTHER PUBLICATIONS

Kyöstiö, S.R. M. et al. (Nov. 1995). "Negative Regulation of the Adeno-Associated Virus (AAV) $P_5$ Promoter Involves Both the $P_5$ Rep Binding Site and the Consensus ATP-Binding Motif of the AAV Rep68 Protein," *J. Virol.* 69(11):6787-6796.

Li, J. et al. (Jul. 1997), "Role for Highly Regulated Rep Gene Expression in Adeno-Associated Virus Vector Production," *J. of Virol.* 71(7):5236-5243.

Li, J. et al. (Mar. 1999), "Synthetic Muscle Promoters: Activities Exceeding Naturally Occuring Regulatory Sequences," *Nat. Biotech.* 17:241-245.

Macejak, D. G. and Sarnow, P. (Sep. 1991), "Internal Initiation of Translation Mediated by the 5' Leader of a Cellular mRNA," *Nature* 353: 90-94.

Magari, S. R. et al. (1997). "Pharmacologic Control of a Humanized Gene Therapy System Implanted into Nude Mice," *J. Clin. Invest.* 100:2865-2872.

Miyatake, S. I. et al. (Jul. 1997). "Transcriptional Targeting of Herpes Simplex Virus for Cell-Specific Replication," *J. of Virol.* 71:5124-5132.

No, D. et al. (Apr. 1996), "Ecdysone-Inducible Gene Expression in Mammalian Cells and Transgenic Mice," *Proc. Natl. Acad. Sci.* 93:3346-3351.

Pelletier, J. and Sonenberg, N. (Jul. 1988). Internal Initiation of Translation of Eukaryotic mRNA Directed by A Sequence Derived From Poliovirus RNA. *Nature* 324:320-325.

Piccioli et al. (Jul. 1991). "Neuroantibodies: Molecular Cloning of a Monclonal Antibody Against Substance P for Expression in the Central Nervous System," *Proc. Natl. Acad. Sci.* 88:5611-5615.

Piccioli, P. et al. (Aug. 1995). "Neurantibodies: Ectopic Expressionof a Recombinant Anti-Substance P Antibody in the Central Nervous System of Transgenic Mice," *Neuron.* 15:373-384.

Rivera, V. M. et al. (Sep. 1996), "A Humanized System for Pharmacologic Control of Gene Expression," *Nat. Medicine* 2(9):1028-1032.

Sandig, V. et al. (1996), "HBV-Derived Promoters Direct Liver-Specific Expression of an Adenovirally Transduced LDL Receptor Gene," *Gene Ther.* 3:1002-1009.

Stein, G.S. et al. (1997). "The Osteocalcin Gene: A Model for Multiple Parameters of Skeletal-Specific Transcriptional Control," *Mol. Biol. Rep.* 24:185-196.

Wang, X. S. and Srivastava, A. (Jun. 1998), "Rescue and Autonomous Replication of Adeno-Associated Virus Type 2 Genomes Containing Rep-Binding Site Mutations in the Viral $P_5$ Promotor," *J. of Virol.* 72(6):4811-4818.

Wang, Y. et al. (Mar. 1997). "Ligand-Inducible and Liver-Specific Target Gene Expression in Transgenic Mice," *Nat. Biotech.* 15:239-243.

Wang, Y. et al. (1997), "Positive and Negative Regulation of Gene Expression in Eukaryotic Cells with an Inducible Transcriptional Regulator," *Gene Ther.* 4:432-441.

Weitzman, M. D. et al. (Mar. 1996), "Recruitment of Wild-Type and Recombinant Adeno-Associated Virus into Adenovirus Replication Centers," *J. of Virol.* 70(3):1845-1854.

Xiao, X, et al. (Mar. 1998), "Production of High-Titer Recombinant Adeno-Associated Virus Vectors in the Absence of Helper Adenovirus," *J. of Virol.* 72(3):2224-2232.

Anderson, J. K. et al. (1993) "Herpesvirus-Mediated Gene Delivery into the Rat Brain: Specificity and Efficiency of the Neuron-Specific Enolase Promoter," *Cell. and Mol. Neurobiol.* 13(5):503-515.

Arbuthnot, P. B. et al. (Aug. 1996). "In Vitro and In Vivo Hepatoma Cell-Specific Expression of a Gene Transferred with an Adenoviral Vector," *Hum. Gene Ther.* 7:1503-1514.

Berns, K. I. and Bohenzky, R. A. (1987). "Adeno-Associated Viruses: An Update," *Advances in Virus Research* 32:243-307.

Boshart, M. et al. (Jun. 1985). "A Very Strong Enhancer is Located Upstream of an Immediate Early Gene of Human Cytomegalovirus," *Cell* 41:521-530.

Carter, B. J. (1990). "The Growth Cycle of Adeno-Associated Virus" Chapter 10 In *CRC Handbook of Parvoviruses.* P. Tijsser ed., CRC Press Inc. 1:155-168.

Chen, J. et al. (1996). "Expression of Rat Bone Sialoprotein Promoter in Transgenic Mia," *J. of Bone and Mineral Research,* 11(5):654-664.

Fisher, K. J. et al. (Jan. 1996). "Transduction with Recombinant Adeno-Associated Virus for Gene Therapy is Limited by Leading-Strand Synthesis," *J. Virol.* 70(1):520-532.

Fisher, K. J. (Nov. 1996). "A Novel Adenovirus-Adeno-Associated Virus Hybrid Vector that Displays Efficient Rescue and Delivery of the AAV Genome," *Hum. Gene Ther.* 7(17):2079-2087.

Gao, G. P. et al. (Nov. 1998). "High-Titer Adeno-Associated Viral Vectors from a Rep/Cap Cell Line and Hybrid Shuttle Virus," *Hum. Gene Ther.* 9:2353-2362.

Gao, G. P. et al. (Dec. 1996). "Biology of Adenovirus Vectors with E1 and E4 Deletions for Liver-Directed Gene Therapy," *J. of Virol.* 70(12):8934-8943.

Gossen, M and Bujard, H. (Jun. 1992). "Tight Controlof Gene Expression in Mammalian Cells by Tetracycline-Responsive Promoters," *Proc. Natl. Acad. Sci.* 89:5547-5551.

Gossen, M. et al. (Jun. 1995). "Transcriptional Activation by Tetracyclines in Mammalian Cells," *Science* 268:1766-1769.

Hansal, S. A. et al. (1998). "Cutting Edge: Inductionof Antigen-Specific Hyporesponsiveness by Transplantion of Hemopoietic Cells Containing an MHC Class I Transgene Regulated by a Lymphocyte-Specific Promoter," *J. of Immunol.* 161:1063-1068.

Hardy, S. (Mar. 1997). "Construction of Adenovirus Vectors Through Cre-Lox Recombination," *J. of Virol.* 71(3):1842-1849.

Harvey, D. M. and Caskey, T. (1998). "Inducible Control of Gene Expression: Prospects for Gene Therapy," *Current Opin. in Chem. Biol.* 2:512-518.

Hirt, B. (1967). "Selective Extraction of Polyoma DNA from Infected Mouse Cell Cultures," *J. Mol. Biol.* 26(2):365-369.

* cited by examiner

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence

```
<220> FEATURE:
<223> OTHER INFORMATION: Primer

<400> SEQUENCE: 1
cgtaaccgag taagatttgg                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
atgttggtgt tggaggtgac                                               20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tggaccagaa atgcaagtcc                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agccttgact gcgtggtggt                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtacctgtat tacttgagca                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
acgagtcagg tatctggtgc                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggactttact gtggacacta                                               20
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gacccagact acgctgacga                                              20
```

PRODUCTION OF RECOMBINANT AAV USING ADENOVIRUS COMPRISING AAV REP/CAP GENES

TECHNICAL FIELD OF THE INVENTION

This invention relates to novel adenoviruses useful in the production of high titers of recombinant adeno-associated virus (rAAV) comprising a foreign DNA insert and methods of making these adenoviruses. The adenovirus comprises the AAV rep gene in which the p5 promoter of rep is replaced by a minimal promoter or by no promoter. The invention also provides methods of producing high levels of rAAV as a substantially homogeneous preparation and compositions of rAAV.

BACKGROUND OF THE INVENTION

A recombinant virus carrying a foreign DNA insert may be used to deliver genes to cells, where the gene may be expressed, if desired, to permit production of recombinant proteins in vitro or in vivo, vaccination of human and non-human mammals, or treatment or amelioration of diseases or genetic defects in humans or in non-human mammals. One may treat or ameliorate diseases or genetic defects by providing some effective level of normal gene products, increased levels of gene products or by blocking endogenous production of a gene, whose expression would be deleterious to the cell or organism.

Methods for delivering an exogenous gene to a mammalian cell include the use of mammalian viral vectors, such as those that are derived from retroviruses, adenoviruses, herpes viruses, vaccinia viruses, polio viruses, adeno-associated viruses, hybrid viruses (e.g., hybrid adenovirus-AAV, see U.S. Pat. No. 5,856,152) and the like. Other methods include direct injection of DNA, biolistic administration of DNA, electroporation, calcium phosphate precipitation, as well as methods of administration which utilize ligand-DNA conjugates, liposome conjugates of DNA, polycation-DNA complexes or adenovirus-ligand-DNA conjugates.

Adeno-associated virus (AAV) systems have many advantages that can be exploited for delivery of transgenes. AAV is a helper-dependent DNA parvovirus which belongs to the genus *Dependovirus*. AAV requires helper function in order for a productive infection to occur. Helper functions may be provided by a number of agents, but generally co-infection with an unrelated helper virus, either adenovirus, herpesvirus or vaccinia, is used. In the absence of such co-infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful co-infection of such cells with a suitable helper virus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243–307.

AAV has a genome of about 4.7 kb in length, including inverted terminal repeats (ITRs) that often, but not necessarily are 145 nucleotides in length. The AAV genome encodes two genes, rep and cap, each of which expresses a family of related proteins from separate open reading frames and which are produced by alternative mRNA splicing and different transcriptional and translational start sites. Rep polypeptides (Rep78, Rep68, Rep52, and Rep40) are involved in replication, rescue and integration of the AAV genome. Rep78 and Rep68 have the same amino-terminal sequence and share the same promoter, p5, but Rep78 contains an exon that is alternatively spliced out in rep68. Similarly, Rep52 and Rep40 have the same amino-terminal sequence and share the p19 promoter, which is downstream from the p5 promoter, but rep52 contains an exon that is alternatively spliced out in rep68. Cap proteins (VP1, VP2, and VP3) form the virion capsid. Cap gene transcription is driven by the p40 promoter. See FIG. 2B for a schematic diagram of the rep and cap genes and promoters p5, p19 and p40. Flanking the rep and cap open reading frames at the 5' and 3' ends of the AAV genome are the ITRs. In certain AAV genomes, the ITRs are 145 nucleotides in length, the first 125 bp of which are capable of forming Y- or T-shaped duplex structures. The entire nucleic acid encoding rep and cap can be excised and replaced with a transgene [B. J. Carter, in "Handbook of Parvoviruses", ed., P. Tijsser, CRC Press, pp. 155–168 (1990)]. The ITRs represent the minimal sequence required for replication, rescue, packaging, and integration of the AAV genome if other sources of rep and cap are provided.

When AAV infects a human cell, the viral genome integrates into chromosome 19 resulting in latent infection of the cell. Upon introduction of helper functions into the cell, such as by infection with a helper virus, the AAV provirus is rescued and amplified. The rescued AAV genomes are packaged into preformed protein capsids (icosahedral symmetry approximately 20 nm in diameter) and released as infectious virions that have packaged either + or − single stranded DNA genomes following cell lysis.

Replacing the rep and cap sequences with a desired transgene yields a rAAV capable of delivering the transgene to target host cells. In current methods, the deleted rep and cap sequences are supplied to the host cells by other viruses or plasmids where they are transiently or stably expressed. There are also a number of cell lines that stably express rep and cap. The host cells also require helper functions in order for the rAAV to replicate and excise from the host cell genome. The helper functions usually are provided by helper viruses (either wildtype or crippled viruses), plasmids containing the helper virus functions or physical methods.

Although it is known that rep is required for replication and excision of AAV, the amount of Rep proteins required for effective rAAV production is, as yet, unclear. U.S. Pat. No. 5,354,678 states that Rep proteins may be toxic to certain cell lines, and WO 97/06272, WO 98/46728 and Li et al. suggest that attenuation of Rep78/68 production results in higher levels of production of rAAV. In contrast, other art, such as U.S. Pat. No. 5,658,776, explicitly states that high expression of Rep proteins—a result of replacing the native p5 promoter with a strong promoter, such as the human immunodeficiency virus long terminal repeat (HIV LTR)— results in high level expression of rAAV. Similarly, U.S. Pat. No. 5,837,484 states that the p5 promoter should be replaced by a strong constitutive promoter or inducible promoter, such as the metallothionein promoter, in order to overcome the strong feedback inhibition by Rep of its own transcription. Thus, U.S. Pat. Nos. 5,658,776 and 5,837,484 suggest that high expression of Rep78/68 is required for efficient rAAV production.

One method that has been used to produce recombinant AAV (rAAV) vectors comprises co-transfecting eukaryotic cells with a plasmid containing rAAV sequences (the cis plasmid) and a plasmid containing rep and cap (the trans plasmid), and infecting the cells with a helper virus (e.g., adenovirus or herpes virus). See U.S. Pat. No. 5,753,500. Li et al. (*J. Virol.* 71:5236–5243, 1997) have modified this method by altering the translation initiation codon of the Rep78/68 proteins in the trans plasmid to decrease the translation of the Rep protein and increase production of rAAV. However, the disadvantage of the methods taught by U.S. Pat. No. 5,753,500 and Li et al. is that co-transfection of two plasmids along with infection by a helper virus is inefficient, may exhibit poor reproducibility, may result in generation of pseudo-wildtype replication-competent AAV (rcAAV), and cannot be easily scaled up for industrial production of rAAV. rcAAV, comprising rep and cap flanked by ITRs, is produced when the rep and cap genes recombine with the ITRs flanking the transgene which results in deletion of the transgene.

A second method that has been used to produce rAAV involves co-transfection of three plasmids into eukaryotic cells. In this method, one plasmid carries the transgene and ITRs (the cis plasmid), a second plasmid encodes the rep and cap genes (the trans plasmid), and the third plasmid encodes the helper virus functions, i.e. adenoviral genes such as E1a, E1b, E2a and E4 (the helper plasmid). The disadvantages of the first method are shared with this method.

A third method involves the use of a packaging cell line such as one including AAV functions rep and cap. See U.S. Pat. Nos. 5,658,785 and 5,837,484 and PCT US98/19463. The packaging cell line may be transfected with a cis plasmid comprising the transgene and ITRs, and infected by wild-type adenovirus (Ad) helper. See U.S. Pat. No. 5,658,785. Alternatively, the packaging cell line may be co-infected by a hybrid Ad/AAV, in which a hybrid Ad vector carries the cis plasmid in the E1 locus (see U.S. Pat. No. 5,856,152), and by a wild-type or mutant Ad that supplies E1. See, e.g., Reference 7. The disadvantage of this method is that it requires making a cell line that expresses sufficient levels of rep and cap, and requires multiple components—including the cell line, the rAAV genome, and an adenovirus—to produce rAAV, which do not lend themselves to easy and convenient downstream manufacturing processes. In addition, some of these packaging cell lines do not produce high levels of rAAV.

A fourth method is provided by a prophetic example in U.S. Pat. No. 5,354,678. The method involves using a recombinant adenovirus in which the rep and cap genes of AAV replace a part of the adenovirus genome not essential for helper virus functions. In this method, an AAV/EBV plasmid vector comprising an rAAV genome is introduced into a cell to produce an rAAV producer cell. It is presumed that the rep gene is driven by its native p5 promoter or by a strong inducible promoter. The recombinant adenovirus comprising rep and cap is then introduced into the cell and their production is induced such that rAAV is produced by the cells. U.S. Pat. No. 5,354,678 does not disclose the levels of rAAV, if any, produced by this method.

As described above, current rAAV production methods are not amenable for production of sufficient rAAV for pharmaceutical applications in a convenient manner. However, the problem of reproducibly generating high levels of substantially homogeneous replication-deficient rAAV by an efficient method that is applicable to large-scale industrial production is solved by the present invention.

SUMMARY OF THE INVENTION

The instant invention provides an alternative production method that results in high yields of rAAV vector and is amenable to large-scale industrial applications. The invention provides a novel adenovirus vector comprising rep and cap genes, thus providing AAV rep and cap and adenovirus helper functions in one component. In the adenovirus vector of the instant invention, the native AAV p5 promoter upstream of rep is removed and replaced with a minimal promoter or with no promoter. This novel vector, when infected into cells containing a nucleic acid sequence comprising a transgene flanked by AAV ITRs, results in the production of high levels of rAAV. The nucleic acid sequence comprising the transgene flanked by AAV ITRs may be established in the host cell by stable integration into the host cell chromosome, secondary infection with an adenovirus or other viral vector carrying the transgene flanked by ITRs (see, e.g, U.S. Pat. No. 5,856,152), infection with an rAAV comprising the transgene, or any other method known in the art, such as transfection, lipofection or microinjection, of plasmid DNA comprising the transgene flanked by ITRs.

In one embodiment of the invention, rep, operably linked to a minimal promoter or to no promoter, is inserted into either the E1 or E3 regions of an adenovirus The adenovirus is deleted in E1 or E3 alone, or a combination of both. In another embodiment, the adenovirus vector is further deleted in E4. In this embodiment, rep sequences may be inserted in E4, while upstream of these rep sequences there may be no promoter or a minimal promoter. In a preferred embodiment, cap is inserted along with the rep gene into the adenoviral vector. In another aspect of the invention, the adenoviral vector comprising the minimal promoter or promoterless rep is used in a method to produce rAAV. The advantage of this method is that it is easily scaled for industrial production of rAAV.

In the method of the invention, the host cell is supplied with an rAAV genome, and the adenovirus comprising the minimal promoter or promoterless rep is infected into the cell. In one embodiment of the invention, the host cell is either simultaneously or sequentially co-infected with two adenoviruses, wherein one adenovirus comprises cap and rep driven from a minimal promoter or no promoter, as described above, and the other adenovirus comprises an rAAV genome. In another preferred embodiment, an adenovirus comprising cap and rep driven from a minimal promoter or no promoter is used to infect a host cell comprising a stably expressed rAAV genome.

In a preferred embodiment of the invention, the method is one in which a high titer of substantially homogeneous rAAV lysates and stocks is achieved.

In any of these embodiments, the host cell may stably express those adenoviral sequences that are deleted from the adenovirus comprising rep and cap. For instance, a cell line such as 293 cells, which express E1, 84-31 cells, which express E1 and E4 (Ref. 1), or 10-3 cells, which express E1 and E4ORF6 (Ref. 11), may be used. Alternatively, a second helper virus is co-infected into the host cell and expresses those adenoviral sequences deleted from the adenovirus comprising rep and cap. For instance, if a second adenovirus comprising a transgene cassette is used to infect the host cell, this adenovirus could supply the deleted adenoviral sequences.

In another embodiment of this invention, the recombinant virus carrying the rep gene may be any virus in which rep interferes with its replication. In this embodiment, the recombinant viral vector comprises a rep gene in which the native p5 promoter of rep is removed and replaced with a minimal promoter or with no promoter.

DETAILED DESCRIPTION OF THE INVENTION

Figure 1:
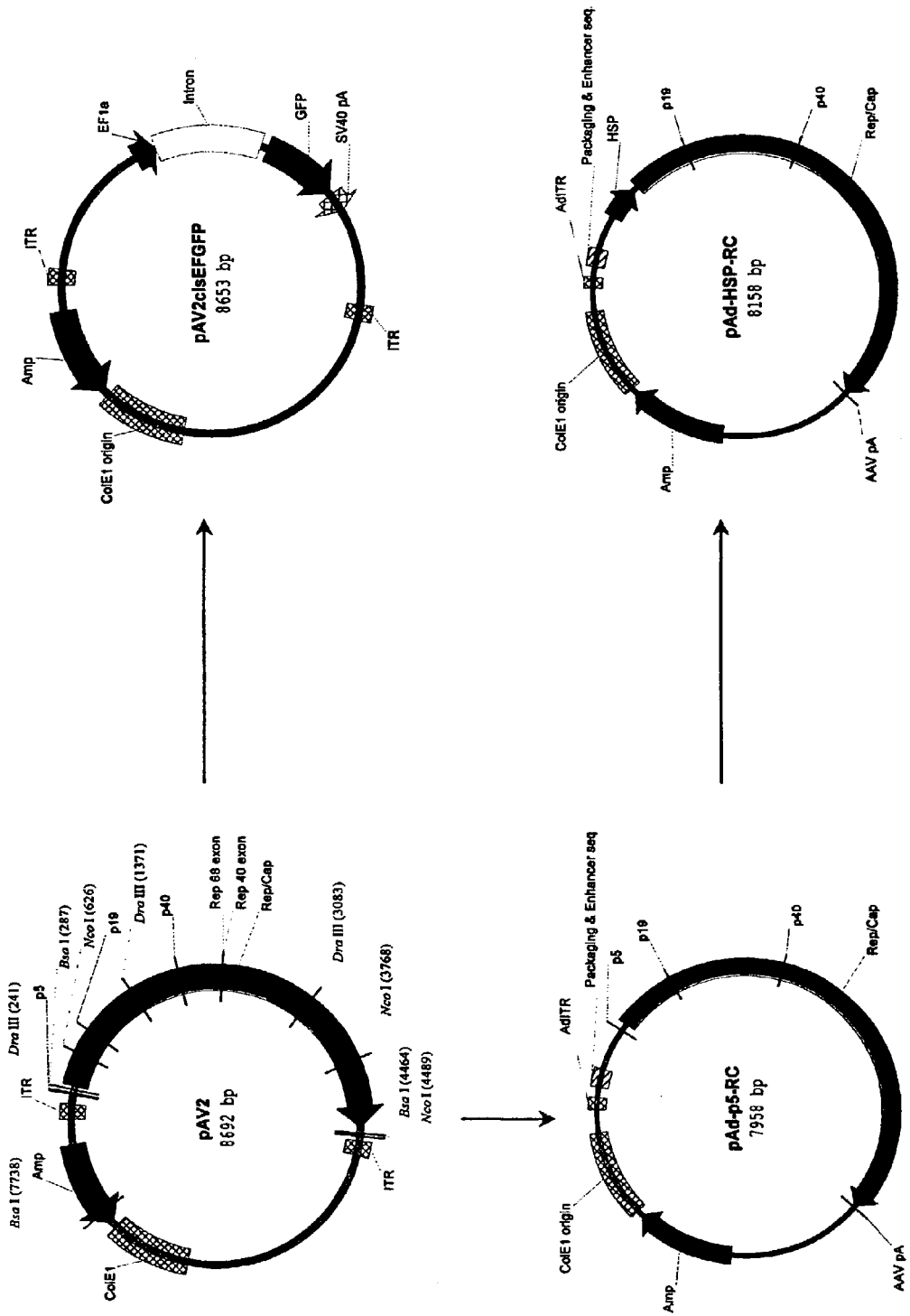
FIG. 1. Construction of recombinant shuttle plasmids pAV2cisEGFP, pAd-p5-RC and pAd-HSP-RC.

The instant invention relates to a novel adenoviral vector and a method for producing high titer stocks of rAAV using this vector. The adenoviral vector comprises a rep gene in which the native AAV p5 promoter upstream of the rep coding sequences has been deleted or effectively rendered inactive by mutation or partial deletion and replaced by a minimal promoter or no promoter.

Although decreasing maximal production of Rep78 and Rep68 may increase rAAV production (see WO 97/06272 and WO 98/46728), there has been no evidence that one could obtain rAAV production if one replaced the p5 promoter with either a minimal promoter that promotes only basal expression of Rep78/68 or with no promoter, i.e., removing the promoter altogether and incorporating rep into an adenovirus.

In a preferred embodiment, Rep78 and Rep68 are produced at much lower levels than Rep52 and Rep40 in 293 cells or other E1-complementing cell lines infected with an adenovirus containing a minimal promoter driving expression of rep78 and rep68. See, e.g., Example 9 and FIG. 10. In another preferred embodiment, host cells are infected with an adenovirus vector comprising a rep gene that lacks any promoter. Although the exact amounts of Rep78 and Rep68 protein expressed in host cells infected by an adenovirus lacking any promoter upstream of rep coding sequences are unknown, it is expected that Rep78 and Rep68 protein levels would be expressed from this recombinant adenovirus at much lower levels than Rep52 and Rep40 or at levels much lower than that expressed by wildtype AAV during infection.

In one embodiment of the invention, the total amount of Rep78 and Rep68 protein is less than 80%, more preferably less than 50%, of the total amount of Rep52 and Rep40 produced in the infected cells. In a more preferred embodiment, the total amount of Rep78 and Rep68 is less than 25% of the total amount of Rep52 and Rep40 produced in the infected cells. In an even more preferred embodiment, the total amount of Rep78 and Rep68 is less than 15%, more preferably 10%, and more preferably is less than 5% of the total amount of Rep52 and Rep40 produced in the infected cells. One may measure the amount of Rep proteins by any method known in the art. These methods include, without limitation, immunoprecipitation of metabolically labeled Rep proteins followed by separation on SDS polyacrylamide gel electrophoresis and quantitation of the labeled protein, enzyme-linked immunosorbent assay (ELISA), radioimmunoassay (RIA), immunofluorescence of infected cells, and quantitative Western blot analysis using radioactive or enzymatic labeling of an anti-Rep antibodies.

Experiments performed using an adenovirus vector comprising a promoterless rep gene demonstrate that the infected host cells also produce rAAV. Without wishing to be bound by any theory, it is possible that in the absence of a promoter upstream of rep, low-level transcription of Rep78 and Rep68 may occur from the upstream ITR of adenovirus or from sequences downstream of the ITR that are upstream of the rep gene.

The instant invention demonstrates that adenoviral vectors comprising a rep gene with its native p5 promoter are unstable when infected into host cells while adenoviral vectors comprising a rep gene with a minimal promoter or no promoter are stably propagated in host cells. See Example 4 and FIGS. 3A and 3B. Example 4 demonstrates that Ad-p5-RC, which is an adenovirus containing p5, rep and cap in the E1 site of the adenovirus vector, undergoes a rearrangement or deletion event in the rep-cap DNA sequences of the adenovirus vector when passaged in 293 cells. In contrast, Ad-HSP-RC, which contains a minimal heat shock protein promoter (HSP), rep and cap, is stable after insertion into the E1 locus of the adenoviral genome and does not appear to undergo any rearrangement when passaged in the same cells. In a preferred embodiment, a minimal promoter or promoterless rep-containing adenovirus of the instant invention is one which is stable upon propagation in a defined host cell system, such as 293 cells.

Figure 8:
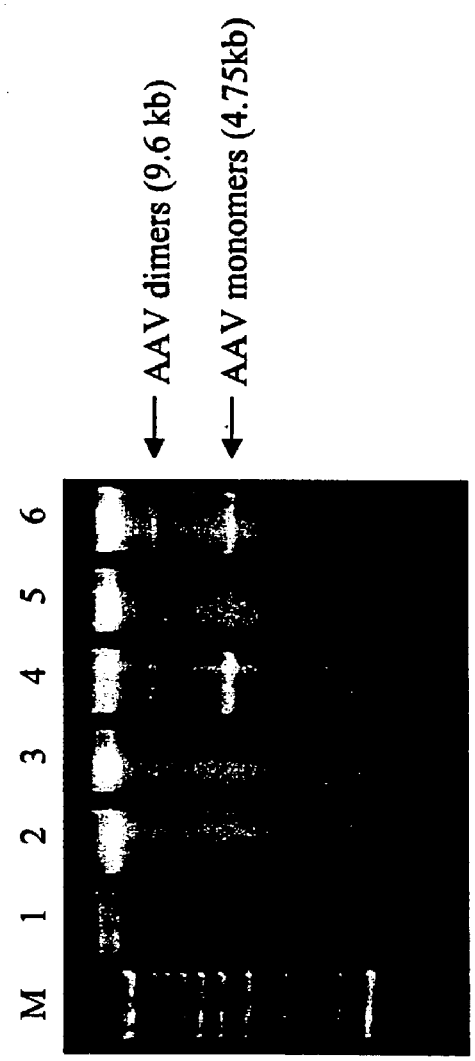
FIG. 8. Ethidium bromide stained agarose gel of Hirt DNA fractionated to detect replicating rAAV DNA in 293 cells (lanes 1–5) or in control B50 cells (lane 6). Lane 1, Ad-p5-RC infection of 293 cells; lane 2, Ad-HSP-RC infection of 293 cells; lane 3, Ad-AAVLacZ infection of 293 cells; lane 4, Ad-HSP-RC and Ad-AAV-LacZ co-infection of 293 cells; lane 5, Ad-p5-RC and Ad-AAV-LacZ co-infection of 293 cells; lane 6, sub100r and Ad-AAV-LacZ stepwise infection of B50 cells. M, 1 kb DNA Ladder size marker (Gibco BRL).
Figure 9:
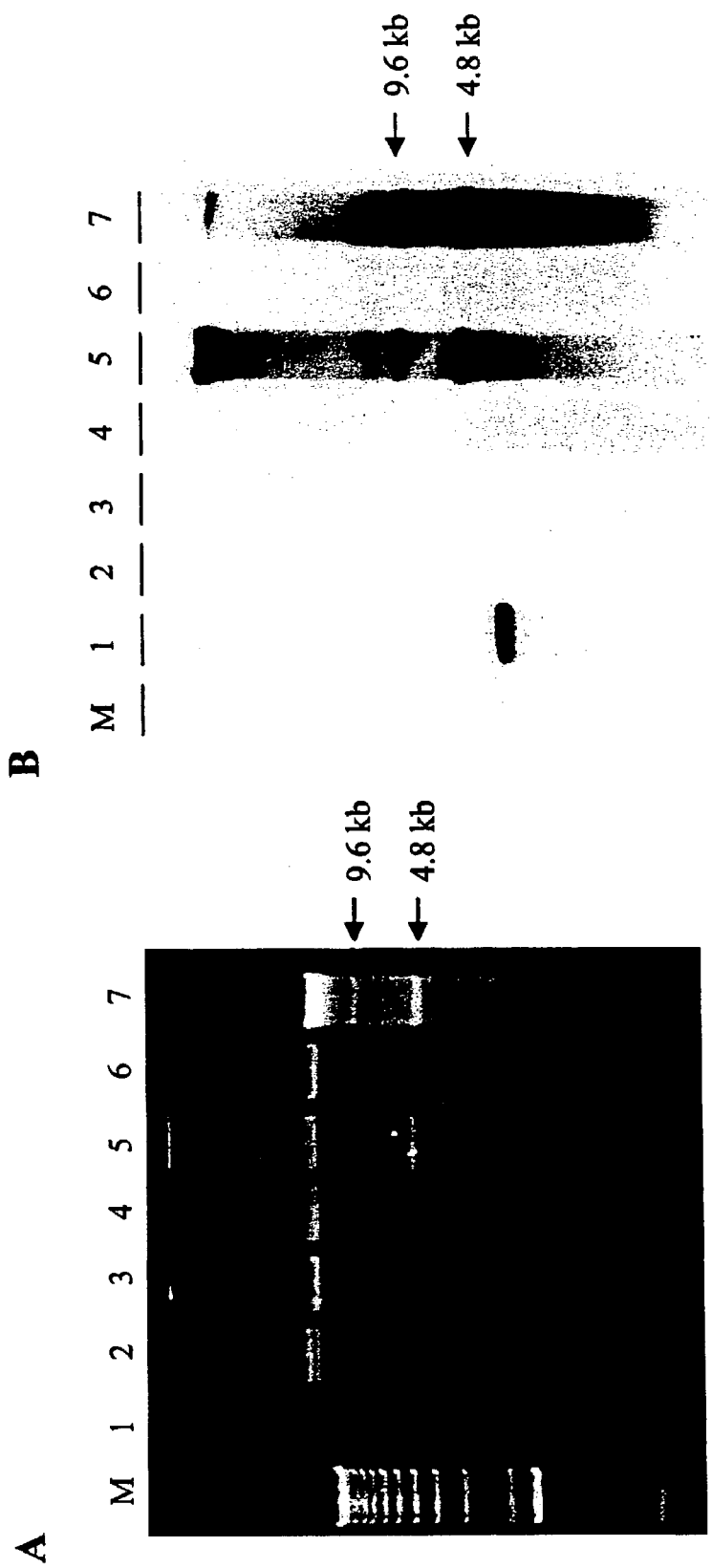
FIG. 9A. Ethidium bromide stained agarose gel of Hirt DNA samples from 293 cells (lanes 2–6) or from control B-50 cells (lane 7) DNA samples.
FIG. 9B. Southern blot analysis of the gel shown in FIG. 9A hybridized to a lacZ DNA probe. Lane 1, lacZ DNA fragment as a positive control; lane 2, Ad-HSP-RC infection of 293 cells; lane 3, Ad-p5-RC infection of 293 cells; lane 4, Ad-AAVLacZ infection of 293 cells; lane 5, Ad-HSP-RC and Ad-AAV-LacZ co-infection of 293 cells; lane 6, Ad-p5-RC and Ad-AAV-LacZ co-infection of 293 cells; lane 7, sub100r and Ad-AAV-LacZ stepwise infection of B50 cells. M, 1 kb DNA Ladder size marker (Gibco BRL)
Figure 10:
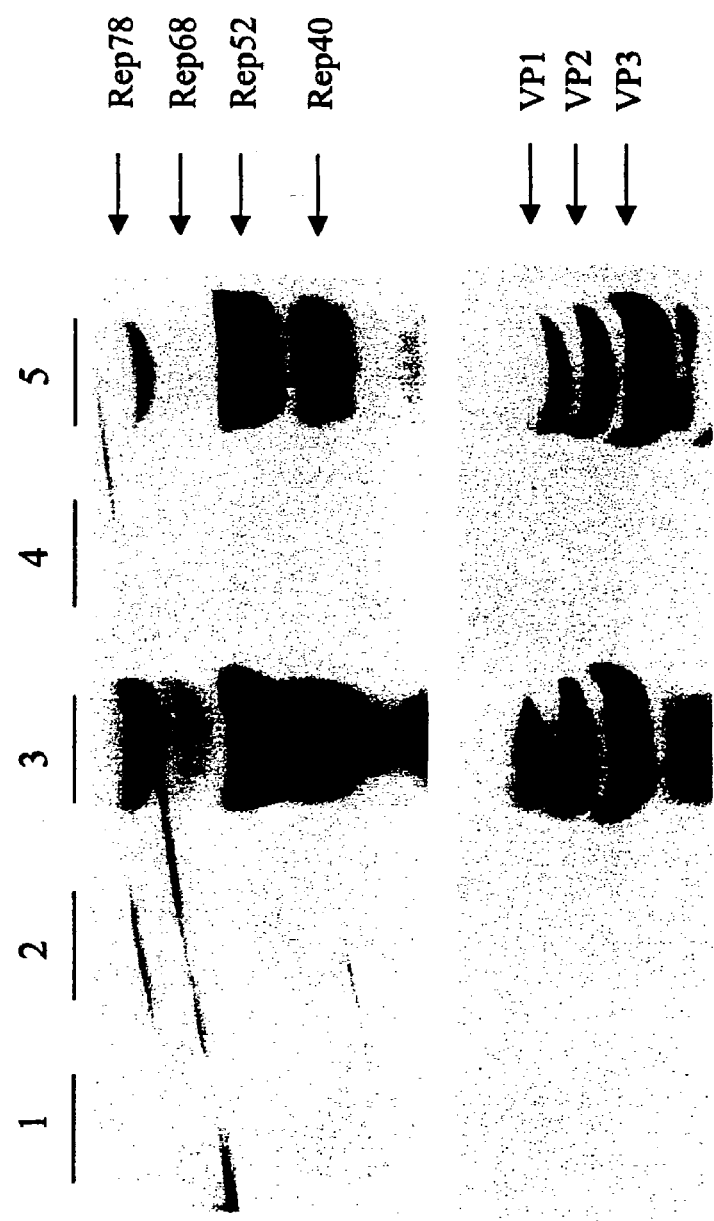
FIG. 10. Western blot analysis of Rep and Cap protein expression in 293 cells infected with or Ad-p5-RC or Ad-HSP-RC viruses. Lane 1, Ad-p5-RC alone; lane 2, Ad-p5-RC+Ad-AAV-LacZ; lane 3, Ad-HSP-RC alone; lane 4, Ad-AAV-LacZ alone; lane 5, Ad-HSP-RC+Ad/AAV-LacZ.

The deletion or rearrangement of rep and cap is further borne out by Examples 8–9 and FIGS. 8–10. Southern blot analysis demonstrates that Hirt DNA from 293 cells co-infected with Ad-HSP-RC and Ad-AAV-LacZ (an adenoviral vector in which a transgene cassette comprising lacZ flanked by AAV ITRs is inserted in E1 of adenovirus) contains LacZ DNA sequences in AAV replicating form (RF) DNA, while Hirt DNA from 293 cells co-infected with Ad-p5-RC and Ad-AAV-LacZ does not contain LacZ DNA sequences in AAV RF DNA. In addition, 293 cells express Rep and Cap proteins when co-infected with Ad-HSP-RC and Ad-AAV-LacZ (see lane 5 of FIG. 10), but do not express these proteins when co-infected with Ad-p5-RC and Ad-AAV-LacZ (see lane 4 of FIG. 10).

The effect of the deletion or rearrangement in Ad-p5-RC is shown by the levels of rAAV produced using this adenovirus vector. Little or no replicating rAAV is produced in cells co-infected with Ad-p5-RC and Ad-AAV-LacZ, while replicating rAAV is observed in 293 cells co-infected with Ad-HSP-RC and Ad-AAV-LacZ. See Example 8 and FIGS. 8, 9A and 9B. Similarly, sufficient amounts of replicating rAAV is produced in cells that have been infected with an adenovirus vector comprising rep sequences downstream of no promoter.

Definitions and General Techniques

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics, virology and immunology. See, e.g., Sambrook et al., 1989, Ausubel et al., 1992, Harlow et al. 1989 (which are incorporated herein by reference).

A "recombinant adeno-associated virus (rAAV) genome" comprises all or a part of an AAV genome, wherein the viral genome may be wild type or may contain point mutations or deletions, and optionally comprises a transgene operably linked to expression control sequences. The transgene may be regulated in cis or in trans. In a preferred embodiment, the rAAV genome comprises a transgene flanked by AAV inverted terminal repeats (ITRs). The rAAV genome of the invention may be embedded in the genome of an adenovirus vector to form a hybrid Ad/AAV. See U.S. Pat. No. 5,586,152, herein incorporated by reference. Alternatively, the rAAV genome may be introduced into a host cell by any route known in the art. The rAAV genome can be expressed transiently or stably in the host cell.

A "recombinant adeno-associated virus" or "rAAV" is the AAV derived from the rAAV genome described above. The rAAV preferably comprises a transgene. The rAAV comprising a transgene is capable of transducing mammalian cells and delivering the transgene thereto.

A "flanking element" or "flanking nucleic acid" is a nucleic acid sequence which, when located in positions flanking a transgene, permits the packaging of the transgene into an rAAV. The flanking elements of AAV are inverted terminal repeats (ITRs). Flanking elements may be the naturally-occurring ITRs from any one of AAV serotypes 1–6 or may be artificial nucleic acid elements, e.g. mutated sequences of ITRs, that have the same or equivalent packaging function.

A "transgene" is a nucleic acid sequence that is to be delivered or transferred to a mammalian cell. A transgene may encode a protein, peptide or polypeptide that is useful as a marker, reporter or therapeutic molecule. The transgene also may be a selection gene, such as one for antibiotic resistance. A transgene may also encode a protein, polypeptide or peptide that is useful for protein production, diagnostic assays or for any transient or stable gene transfer in vitro or in vivo. Alternatively, a transgene may not encode a protein but rather be used as a sense or antisense molecule, ribozyme or other regulatory nucleic acid to modulate replication, transcription or translation of a nucleic acid to which it is complementary or to target a complementary mRNA for degradation.

"Expression control sequences" are nucleic acid sequences that regulate the expression of a gene by being operably linked to the gene of interest.

"Operably linked" sequences include both expression control sequences that are contiguous with the gene of interest and expression control sequences that act in trans or at a distance to control the gene of interest Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion.

A "transgene cassette" is a nucleic acid sequence comprising a transgene operably linked to expression control sequences in which the transgene and expression control sequences are flanked by AAV flanking sequences. In a preferred embodiment, the flanking sequences are AAV ITRs.

An "adenovirus genome" is the nucleic acid molecule backbone of an adenovirus particle. The adenovirus genome may contain point mutations, deletions or insertions of nucleotides. The adenovirus genome may further comprise a foreign gene.

An "adenovirus" is an encapsidated adenovirus genome capable of binding to a mammalian cell and delivering the adenovirus genome to the cell's nucleus. The term "adenovirus" encompasses both recombinant and non-recombinant adenoviruses. The term "adenovirus" also encompasses both wildtype and mutant adenoviruses.

A "recombinant adenovirus" is an adenovirus which contains one or more genes that are foreign to a wildtype adenovirus. Recombinant adenoviruses include, without limitation, those that include foreign genes such as rep and/or cap, as well as adenoviruses that comprise an rAAV genome.

An "adenovirus vector" is a recombinant adenovirus comprising one or more foreign genes, wherein the adenovirus vector is capable of binding to a mammalian cell and delivering the foreign gene to the cell's nucleus. The foreign genes include, without limitation, genes such as rep and cap, rAAV genomes, such as transgenes and expression control sequences, or any foreign gene that is useful in increasing production of rAAV.

A "locus" is a site within a virus wherein a particular gene normally resides. For instance, the "adenovirus E1 locus" is the site at which E1 resides in adenovirus. If a foreign gene or nucleic acid is inserted into a locus, it may either replace the gene that resides there or it may be inserted at the site in addition to the gene that resides there.

An "AAV p5 promoter" or "p5 promoter" is one that is derived from any AAV serotype, including AAV Serotypes 1 to 6, as well as any AAV that infects non-human species, such as avian and bovine AAV. The p5 promoter of AAV-2 directs the expression of rep78 and rep68, and is downregulated by the Rep protein, and is upregulated by certain adenoviral proteins, including E1.

As used herein, the term "deleted p5 promoter" refers to a p5 promoter that has been completely deleted from the AAV genome or to a p5 promoter that has been effectively deleted or attenuated such that the p5 promoter is less active when compared to the wildtype p5 promoter in promoting transcription in a cell into which it has been introduced. The p5 promoter may be effectively deleted or attenuated by any method, including, without limitation, removing or mutating a sufficient number of nucleotides to render the p5 promoter less active or inactive or moving the promoter relative to the coding sequences of rep such that the promoter is less active. In an alternative embodiment, one may increase the distance between the p5 promoter and the start codon of the rep gene to decrease promoter activity. For instance, one may move the p5 promoter downstream of the rep gene or insert nucleotide sequences between the p5 promoter and the downstream ATG start codon. One may measure whether a p5 promoter is effectively deleted by measuring the transcription of a gene operably linked to the mutated or partially deleted p5 promoter and comparing the gene's transcription to the transcription of a gene in a promoterless construct.

In a preferred embodiment, a p5 promoter is effectively deleted when it promotes less than 80% of wildtype p5 promoter activity, more preferably less than 50% of wildtype p5 promoter activity. In a more preferred embodiment, a p5 promoter is effectively deleted when it promotes less than 25% of wildtype p5 promoter activity. In an even more preferred embodiment, a p5 promoter is effectively deleted when it promotes less than 15%, more preferably promotes less than 10%, and more preferably less than 5% of wildtype p5 promoter activity. In another preferred embodiment, a p5 promoter is effectively deleted when the rep gene to which it is operably linked is not rearranged or deleted when an adenovirus comprising the effectively deleted p5 promoter and rep gene is infected into a host cell, such as 293 cells. In another preferred embodiment, a p5 promoter is effectively deleted when a host cell infected with an adenovirus comprising rep and the deleted p5 promoter produces rAAV at a high titer. In a preferred embodiment, the titer is at least $10^2$ particles per cell; preferably at least $10^3$ particles per cell; more preferably at least $10^4$ particles per cell; and, even more preferably, at least $10^5$ or $10^6$ particles per cell. In general, there are approximately $1 \times 10^3$ to $3 \times 10^3$ particles per transducing units (TU). The number of particles required to produce one TU varies based upon the transgene, purification method and assay method.

A "minimal promoter" is one that essentially comprises only a TATA box and promotes only very low or basal levels of transcription of rep78 and rep68. A promoter is a nucleotide sequence that promotes the initiation of transcription at a particular site by the cell's transcriptional machinery.

In a preferred embodiment, a minimal promoter promotes transcription that is less than 80% of the wildtype p5 promoter, more preferably less than 50% of the wildtype p5 promoter, even more preferably less than 25% of the wildtype p5 promoter. In a more preferred embodiment, a minimal promoter is one that promotes transcription that is less than 20% of the wildtype p5 promoter, even more preferably less than 15% of the wildtype p5 promoter. In an even more preferred embodiment, a minimal promoter is one that promotes transcription that is less than 10% of the wildtype p5 promoter, even more preferably less than 5%, even more preferably less than 1% of the wildtype p5 promoter.

A minimal promoter also may be defined by functional measures. A minimal promoter is one in which the rep gene to which it is operably linked is not rearranged or deleted when an adenovirus comprising the minimal promoter and rep gene is infected into a host cell, such as 293 cells. A minimal promoter is one in which a host cell infected with an adenovirus comprising a minimal promoter that regulates transcription of rep78 and rep68 produces rAAV at a high titer. In a preferred embodiment, the titer is at least $10^2$ particles per cell, preferably at least $10^3$ particles per cell; more preferably at least $10^4$ particles per cell; and, even more preferably, at least $10^5$ or $10^6$ particles per cell.

Many minimal promoters are known in the art. Alternatively, an artificial minimal promoter may be constructed by using a sequence or a consensus sequence of a TATA box and adding nucleotide sequences to the 5' and 3' ends of the TATA box. The activity of the minimal promoter may be measured by measuring the transcription of the artificial minimal promoter and comparing it to an natural minimal promoter, such as the *Drosophila* heat shock protein promoter.

Rep78/68 is "promoterless" or has "no promoter" when the p5 promoter has been deleted or effectively deleted, as defined supra, and no promoter has been inserted in its place. Alternatively, rep78/68 is promoterless when the p5 promoter has been deleted and is replaced by a heterologous promoter that does not promote transcription in the host cell in which the adenovirus has been infected. For instance, rep78/68 would be considered promoterless if p5 were substituted by a promoter that was active in bacterial or insect cells, for example, but that was inactive in a mammalian host cell. In another embodiment, rep78/68 is promoterless when the p5 promoter has been deleted and replaced by an inducible promoter that permits low-level expression of rep78/68.

The Adenoviral Vector

A large number of adenoviruses and adenoviral vectors are known, including human adenoviruses types 1–46, chimpanzee adenoviruses, canine adenoviruses, bovine adenoviruses [all available from the American Type Culture Collection (ATCC), 10801 University Boulevard, Manassas, Va. 20110-2209], and ovine adenoviruses (Both et al., WO 97/06826 A1). Any of these adenoviruses may be used in this invention, provided that the adenovirus is able to infect the target host cell. For instance, a human adenovirus would generally be used to infect a human cell, while a bovine adenovirus would be used to infect a bovine cell.

In one embodiment, the adenoviral vector comprises the AAV rep gene downstream of a minimal promoter or no promoter (this is alternatively referred to as a minimal promoter or promoterless AAV rep gene), and sufficient helper virus functions for rAAV production in a host cell. In a preferred embodiment, the adenoviral vector further comprises the AAV cap gene. The type of adenoviral sequences required for replication and encapsidation of the rAAV genome depends upon whether the host cell expresses any helper functions or whether other vectors or viruses are introduced into the host cell which express helper functions. For instance, if the adenovirus is to be used to infect a cell line that expresses E1, e.g., the 293 cell line, then the adenoviral vector could comprise rep and cap, and could also comprise those helper virus functions required in addition to E1 (e.g., E2a, E4ORF6 and VAI RNA). If the adenovirus is used to infect a cell line such as 84-31, which expresses E1 and E4, then the adenoviral vector could express rep, cap, E2a and VAI RNA. If the adenovirus is used to infect a cell line that does not express any helper functions, then the adenovirus vector could comprise, at least, E1 (both E1a and E1b) and E2a, and, optionally, may comprise E4ORF6 and VAI RNA. In an alternative embodiment, helper functions may be supplied by chemical or physical methods or by other helper viruses.

The recombinant adenovirus comprising the rep gene downstream of a minimal promoter or no promoter may be produced by any method known in the art. In one preferred method, the recombinant adenovirus of the instant invention is produced using homologous recombination. In another preferred method, the recombinant adenovirus is produced using Cre-lox recombination (12).

In an alternative embodiment, some or all of the helper virus functions may be provided by nucleic acid sequences that are introduced into the host cell. For instance, the host cell may be co-infected with a second virus, such as an adenovirus, that expresses some or all of the required helper functions. In a preferred embodiment, a second adenoviral vector comprises a transgene cassette and further comprises helper functions that are not expressed by either the host cell or the adenovirus comprising the rep gene. See, e.g., Examples 6–8. Alternatively, some or all of the helper virus functions may be provided by any method known in the art, such as by transfection or direct injection, as discussed above.

Based on this description, other embodiments of the adenoviral vector will be readily apparent to those of ordinary skill in the art. Other viral vectors in which Rep interferes with viral replication also may be used.

Rep and Cap Nucleic Acids

In AAV's life cycle, both rep and cap are required for excision, replication and encapsidation of the recombinant viral genome into an infectious recombinant vector or virus. The Rep and Cap proteins may have a naturally occurring sequence derived from any serotype of AAV, including serotypes 1 to 6. In one preferred embodiment, the rep and cap genes are derived from the same AAV serotype. In another preferred embodiment, the rep and cap genes are derived from different AAV serotypes to permit the production a pseudotyped rAAV. Pseudotyped rAAV is desirable in cases in which the rAAV is to be administered to a patient as a gene therapy vector and there are existing neutralizing antibodies in the patient's serum to the capsid proteins of one AAV serotype and not to another AAV serotype. The cap gene from the serotype to which there is an antibody response may be exchanged by the cap gene from a different serotype of AAV to which there is no antibody response. For example, the rep gene from AAV-2 may be used with the cap gene from AAV-1 to produce a pseudotyped rAAV-2, or vice-versa.

In an alternative embodiment, the Rep and/or Cap proteins may have a mutated sequence, including insertions, deletions, fragments or point mutations of particular amino acid residues, so long as the mutated Rep and/or Cap proteins retain their respective excision, replication and encapsidation functions. In a preferred embodiment, the naturally-occurring Rep and Cap amino acid sequences from AAV-2 are used. In one embodiment, a single adenovirus comprises the nucleic acid sequences encoding the Rep and Cap proteins. In another embodiment, the nucleic acid sequences encoding the Rep and Cap proteins are inserted at a single site within one adenovirus, e.g., both rep and cap are inserted at E1, E3 or E4 of adenovirus. Alternatively, the nucleic acid sequences encoding Rep and Cap, respectively, are each inserted at different loci in the adenovirus genome, e.g., the nucleic acid sequence encoding Rep may be in E1, and the nucleic acid sequence encoding Cap may be in E4, and other combinations thereof. Alternatively, a cell line comprising the cap gene may be used, in which case only the rep gene would be required on the adenoviral vector. See, e.g., WO 98/27204.

The minimal promoter that regulates expression of Rep78 or Rep68 may be any promoter that promotes only basal expression of the rep gene in a host cell. In general, the promoter is one that essentially contains a TATA box as its only regulatory element. In a preferred embodiment, the minimal promoter is the *Drosophila* heat shock promoter (HSP). In another preferred embodiment, the minimal promoter is the minimal promoter derived from the adenovirus E1b gene that provides only basal promoter activity. In another preferred embodiment, the minimal promoter is a 70 nucleotide DNA element derived from the promoter region upstream of the adenovirus pIX gene. The minimal pIX promoter comprises a TATA box and an Sp1 box, and, in Ad5, corresponds to nucleotides 3511 to 3580. Many other adenovirus serotypes contain the pIX gene and its upstream promoter as well, and the minimal promoters derived from these pIX promoters are encompassed by this invention as well. Other minimal promoters are well known in the art and may be used in the practice of this invention. In another preferred embodiment, the p5 promoter is deleted altogether and replaced by no promoter at all.

In another embodiment of the invention, the activity of the Rep78/68 proteins are attenuated by mutating the rep78/68 genes to produce Rep78/68 proteins that are less active than wildtype Rep78/68. This may be done by altering the coding sequence of the Rep78/68 proteins to make them less active. Alternatively, one may alter the DNA sequence of rep78/68 to destabilize the RNA encoded by the gene and thus decrease the amount of Rep78/68 proteins produced.

One may determine whether a DNA sequence is appropriate for use as a minimal promoter by inserting the DNA sequence upstream of the rep78/68 ATG codon in a plasmid construct or an adenoviral vector and transfecting or infecting, respectively, a host cell that comprises an rAAV genome, incubating the host cell under conditions in which rAAV is produced, measuring the titer of rAAV produced, and comparing the titer to that produced using a control plasmid or adenovirus comprising a rep gene whose expression is regulated by a minimal promoter. The host cell may comprise the rAAV genome stably or transiently. Alternatively, one may measure the level of Rep78 and Rep68 produced in the host cell after infection to determine if sufficiently low levels of Rep78 and Rep68 are produced.

Helper Functions

As discussed above, AAV requires helper functions for excision, replication and encapsidation of AAV. AAV helper functions can be provided by adenovirus, herpesvirus [including herpes simplex virus type 1 (HSV-1) or type 2 (HSV-2), cytomegalovirus (CMV) and pseudorabies virus (PRV)] or by exposure of the cells to different chemical or physical agents. Alternatively, one of skill in the art may determine which helper functions are required by producing rAAV using the compositions and methods disclosed in the instant specification.

To identify which helper functions are required for high levels of rAAV production, one may transfect a host cell containing an rAAV genome with a plasmid comprising rep and cap and then transfect with one or nucleic acids encoding various potential helper functions to determine which potential helper functions are required for rAAV production. The rAAV genome may be stably integrated into the host cell or may be transfected or infected into the host cell by methods known in the art. After transfecting the host cell with the nucleic acid encoding the potential helper function, one may then measure the titer of the rAAV that is produced to determine if the nucleic acid encodes a helper function.

In a preferred embodiment, the helper functions are nucleic acids derived from a virus. In a more preferred embodiment, the helper functions are derived from adenovirus types 2 or 5, HSV-1, HSV-2, CMV or PRV. In an even more preferred embodiment, the helper functions are E1a, E1b, E2a, E4ORF6 proteins and VAI RNA from adenovirus. In another preferred embodiment, the nucleic acid encodes the helper functions from the helicase-primase complex of HSV (UL5, UL8 and UL52) and the major single-stranded DNA binding protein of HSV (UL29). Alternatively, helper functions for recombinant AAV may be provided by chemical or physical agents, including ultraviolet light, cycloheximide, hydroxyurea and various carcinogens.

The required helper functions for production of a rAAV may be delivered to the host cell by any method known in art. The helper functions may be delivered by transfection with a vector, such as a plasmid, by infection with a viral vector comprising the helper functions, or by any other method known in the art, including those discussed above (e.g., biolistic injection of DNA, use of DNA conjugates, etc.). The transfection or infection may be stable or transient. Alternatively, the cell line may stably express (either on an extrachromosomal episome or through integration in the cell's genome) the helper functions. In addition, some of the helper functions may be expressed by the mammalian cell line while other helper functions are introduced by a vector. Thus, for production of rAAV in 293 cells (ATCC CRL-1573), which constitutively produce adenoviral E1a and E1b proteins, only E2a, E4ORF6 and VAI must be introduced into the host cell by transfection or infection of a vector.

In a preferred embodiment, the helper functions are transduced into the host cells by an adenovirus. In a more preferred embodiment, some or all of the helper functions are transduced into the host cell by the adenovirus that comprises the rep and/or cap genes. In a preferred embodiment, the native helper function sequences are used. However, mutated helper function sequences may be used so long as they retain their helper function activity. The helper function nucleic acids may be supplied with its native promoter or may be under the regulatory control of a variety of promoters, constitutive or inducible, such as the CMV immediate-early promoter/enhancer or the zinc-inducible metallothionein promoter, respectively, as known in the art or as described above.

The rAAV Transgene Cassette

In order to manufacture a rAAV containing a transgene, the method of the present invention begins with a desired transgene, then associates the transgene with appropriate expression regulatory sequences (ERS), e.g., promoter, enhancer, polyadenylation site, then inserts this ERS-transgene construct between AAV flanking sequences, e.g., the ITRs, in place of rep and cap genes normally found therein. Where the length of the ERS-transgene cassette is shorter than the AAV rep and cap sequences, and that shorter length would pose an obstacle to proper packaging, an optional spacer or "stuffer" sequence may be inserted in order to maintain the proper length for packaging. The transgene cassette comprised of the ERS-transgene bordered by the AAV flanking sequences may then be embedded in an adenovirus vector separate from that which carries the rep gene. Alternatively, the transgene cassette may be inserted into a plasmid vector and transfected into a host cell. The transgene cassette may be maintained in the host cell stably, either by integration into the host cell genome or as an episome, or may be introduced transiently, such as by infection with a hybrid Ad/AAV virus. See, e.g., Examples 3 and 6–8. Each element of the transgene cassette is further described below:

The Transgene

A transgene is a nucleic acid encoding a protein of interest; it may be a gene to allow for genetic or drug selection, e.g., a gene conferring resistance to antibiotics, or a reporter gene allowing detection, e.g., by color in the case of the use of green fluorescent protein. Alternatively, the transgene may be one that is useful for corrective applications. For instance, a transgene may be a normal gene that replaces or augments the function of a patient's defective gene. The transgene may be one that counteracts the effects of a disease, such as introduction and expression of a gene that is distinct from the one that it replaces or augments, but which has the same function or compensates for the defective gene's function. The transgene may be a gene which blocks or represses the expression of a malfunctioning, mutated, or viral gene in the patient, thereby giving rise to a corrective effect. A transgene may also be a protective gene, such as one that prevents cellular apoptosis, injury, toxicity or death. A transgene may also be used for immunization against various agents, by provoking an immunogenic response in an animal. Delivery of therapeutic transgenes to a patient thus effects some level of correction of a defect or is beneficial for prevention of disease. The transgene also may be a gene which would confer sensitivity to a reagent that results in cellular toxicity, e.g., introduction of HSV thymidine kinase, which confers sensitivity to gancyclovir. The transgene also may be one which is useful for production of proteins in vitro, such as for large-scale production of therapeutic proteins.

Many gene therapy methods involve supplying an exogenous gene to overcome a deficiency in the expression of a gene in a patient. Some of these deficiencies are congenital and are due to a mutation in a particular gene in all the cells of the patient. For instance, in cystic fibrosis, there are one or more mutations in the gene encoding the cystic fibrosis transmembrane conductance regulator (CFTR) which prevents the CFTR protein from functioning properly. In other cases, a deficiency in gene expression is due to an accident or disease that occurs during the patient's life. For instance, in Type I diabetes mellitus, the β pancreatic islet cells, which produce insulin, are destroyed, such that patients with this disease can no longer synthesize insulin. In other cases, the endogenous gene may be structurally normal but is not transcribed and/or translated in high enough quantities due to disease, medical treatment or other environmental conditions, or mutations in the regulatory elements of the endogenous gene. For example, there are a number of blood disorders, such as anemia, in which there is insufficient production of red blood cells, which may be treated with erythropoietin (EPO) or with a transgene encoding EPO. Conversely, gene therapy methods may be used where overexpression of a particular gene results in a disease state. For instance, overexpression of c-myc by the immunoglobulin heavy chain promoter results in leukemia. Transgenes may also be used for genetic immunization, i.e., to elicit an immune response to a pathogen in an animal, including humans. For instance, a transgene may include a sequence from a viral, bacterial or fungal pathogen, such as influenza virus, human immunodeficiency virus (HIV), or *mycobacterium tuberculosis*.

Appropriate genes for expression in the cell include, without limitation, those genes which are normally expressed in cells but whose products are produced in abnormal amounts due to over- or under-expression. Alternatively, the appropriate gene for expression is one which expresses a normal gene product which replaces a defective gene product, encodes ribozymes or antisense molecules which repair or destroy mutant cellular RNAs expressed from mutated genes, or modifies or destroys viral RNAs. Transgenes used for production of proteins in vitro include proteins such as secreted factors, including hormones, growth factors and enzymes.

The composition of the transgene sequence depends upon the intended use for the resulting rAAV. For example, one type of transgene sequence comprises a reporter or marker sequence, which upon expression produces a detectable signal. Such reporter or marker sequences include, without limitation, DNA sequences encoding *E. coli* β-lactamase, β-galactosidase (LacZ), alkaline phosphatase, HSV thymidine kinase, green fluorescent protein (GFP), bacterial chloramphenicol acetyltransferase (CAT), firefly luciferase, eukaryotic membrane bound proteins including, for example, CD2, CD4, CD8, the influenza hemagglutinin protein, and others well known in the art, to which high affinity antibodies directed to them exist or can be made routinely, and fusion proteins comprising a membrane bound protein appropriately fused to an antigen tag domain from, among others, hemagglutinin or myc.

These sequences, when associated with regulatory elements which drive their expression, provide signals detectable by conventional means, including enzymatic, radiographic, calorimetric, fluorescence or other spectroscopic assays, fluorescent activated cell sorting assay and immunological assays, including ELISA, RIA and immunohistochemistry. For example, where the transgene is the LacZ gene, the presence of a rAAV is detected by assays for β-galactosidase activity. Similarly, where the transgene is luciferase, the rAAV gene expression may be measured by light production in a luminometer.

However, desirably, the transgene is a non-marker gene which can be delivered to a cell or an animal via the rAAV produced by this method. The transgene may be selected from a wide variety of gene products useful in biology and medicine, such as proteins, sense or antisense nucleic acids (e.g., RNAs), or catalytic RNAs. The invention may be used to correct or ameliorate gene deficiencies, wherein normal genes are expressed but at greater than normal or less than normal levels, and may also be used to correct or ameliorate genetic defects wherein a functional gene product is not expressed. A preferred type of transgene sequence is a therapeutic gene which expresses a desired corrective gene product in a host cell at a level sufficient to ameliorate the disease, including partial amelioration. These therapeutic nucleic acid sequences typically encode products which, upon expression, are able to correct, complement or compensate an inherited or non-inherited genetic defect, or treat an epigenetic disorder or disease. However, the selected transgene may encode any product desirable for study. The selection of the transgene sequence is not a limitation of this invention. Choice of a transgene sequence is within the skill of the artisan in accordance with the teachings of this application.

The invention also includes methods of producing rAAV and compositions thereof which can be used to correct or ameliorate a gene defect caused by a multi-subunit protein. In certain situations, a different transgene may be used to encode each subunit of the protein. This may be desirable when the size of the DNA encoding the protein subunit is large, e.g., for an immunoglobulin or the platelet-derived growth factor receptor. In order for the cell to produce the multi-subunit protein, a cell would be infected with rAAV expressing each of the different subunits.

Alternatively and more preferably, different subunits of a protein may be encoded by the same transgene. In this case, a single transgene would include the DNA encoding each of the subunits, with the DNA for each subunit separated by an internal ribosome entry site (IRES). The use of IRES permits the creation of multigene or polycistronic mRNAs. IRES elements are able to bypass the ribosome scanning model of 5' methylated cap-dependent translation and begin translation at internal sites (Pelletier and Sonenberg, 1988). For example, IRES elements from hepatitis C and members of the picornavirus family (e.g., polio and encephalomyocarditis) have been described, as well an IRES from a mammalian mRNA (Macejak and Sarnow, 1991). IRES elements can be linked to heterologous open reading frames. By virtue of the IRES element, each open reading frame is accessible to ribosomes for efficient translation. Thus, multiple genes can be efficiently expressed using a single promoter/enhancer to transcribe a single message. This is preferred when the size of the DNA encoding each of the subunits is sufficiently small that the total of the DNA encoding the subunits and the IRES is no greater than the maximum size of the DNA insert that the virus can encompass. For instance, for rAAV, the insert size can be no greater than approximately 4.8 kilobases; however, for an adenovirus which lacks all of its helper functions, the insert size is approximately 28 kilobases.

Useful gene products include hormones and growth and differentiation factors including, without limitation, insulin, glucagon, growth hormone (GH), parathyroid hormone (PTH), calcitonin, growth hormone releasing factor (GRF), thyroid stimulating hormone (TSH), adrenocorticotropic hormone (ACTH), prolactin, melatonin, vasopressin, β-endorphin, met-enkephalin, leu-enkephalin, prolactin-releasing factor, prolactin-inhibiting factor, corticotropin-releasing hormone, thyrotropin-releasing hormone (TRH), follicle stimulating hormone (FSH), luteinizing hormone (LH), chorionic gonadotropin (CG), vascular endothelial growth factor (VEGF), angiopoietins, angiostatin, endostatin, granulocyte colony stimulating factor (GCSF), erythropoietin (EPO), connective tissue growth factor (CTGF), basic fibroblast growth factor (bFGF), bFGF2, acidic fibroblast growth factor (aFGF), epidermal growth factor (EGF), transforming growth factor α (TGFα), platelet-derived growth factor (PDGF), insulin-like growth factors I and II (IGF-I and IGF-II), any one of the transforming growth factor β (TGFβ) superfamily comprising TGFβ, activins, inhibins, or any of the bone morphogenic proteins (BMP) BMPs 1–15, any one of the heregulin/neuregulin/ARIA/neu differentiation factor (NDF) family of growth factors, nerve growth factor (NGF), brain-derived neurotrophic factor (BDNF), neurotrophins NT-3, NT-4/5 and NT-6, ciliary neurotrophic factor (CNTF), glial cell line derived neurotrophic factor (GDNF), neurtuin, persephin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-1β, IL-2, IL-3, IL-4, IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), granulocyte colony stimulating factor (G-CSF), monocyte colony stimulating factor (M-CSF), Fas ligand, tumor necrosis factors α and β (TNFα and TNFβ), interferons (IFN) IFN-α, IFN-β and IFN-γ, stem cell factor, flk-2/flt3 ligand. Gene products produced by the immune system are also encompassed by this invention. These include, without limitations, immunglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Useful gene products also include complement regulatory proteins such as membrane cofactor protein (MCP), decay accelerating factor (DAF), CR1, CR2 and CD59.

Still other useful gene products include any one of the receptors for the hormones, growth factors, cytokines, lymphokines, regulatory proteins and immune system proteins. Examples of such receptors include flt-1, flk-1, TIE-2; the trk family of receptors such as TrkA, MuSK, Eph, PDGF receptor, EGF receptor, HER2, insulin receptor, IGF-1 receptor, the FGF family of receptors, the TGFβ receptors, the interleukin receptors, the interferon receptors, serotonin receptors, α-adrenergic receptors, β-adrenergic receptors, the GDNF receptor, p75 neurotrophin receptor, among others. The invention encompasses receptors for extracellular matrix proteins, such as integrins, counter-receptors for transmembrane-bound proteins, such as intercellular adhesion molecules (ICAM-1, ICAM-2, ICAM-3 and ICAM-4), vascular cell adhesion molecules (VCAM), and selectins E-selectin, P-selectin and L-selectin. The invention encompasses receptors for cholesterol regulation, including the LDL receptor, HDL receptor, VLDL receptor, and the scavenger receptor. The inventions encompasses the apolipoprotein ligands for these receptors, including ApoAI, ApoAIV and ApoE. The invention also encompasses gene products such as steroid hormone receptor superfamily including glucocorticoid receptors and estrogen receptors, Vitamin D receptors and other nuclear receptors. In addition, useful gene products include antimicrobial peptides such as defensins and maginins, transcription factors such as jun, fos, max, mad, serum response factor (SRF), AP-1, AP-2, myb, MRG1, CREM, Alx4, FREAC1, NF-κB, members of the leucine zipper family, C2H4 zinc finger proteins, including Zif268, EGR1, EGR2, C6 zinc finger proteins, including the glucocorticoid and estrogen receptors, POU domain proteins, exemplified by Pit 1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor 1 (IRF-1), Wilms tumor protein, ETS-binding protein, STAT, GATA-box binding proteins, e.g., GATA-3, and the forkhead family of winged helix proteins.

Other useful gene products include carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, porphobilinogen deaminase, factor VII, factor VIII, factor IX, factor II, factor V, factor X, factor XII, factor XI, von Willebrand factor, superoxide dismutase, glutathione peroxidase and reductase, heme oxygenase, angiotensin converting enzyme, endothelin-1, atrial natriuetic peptide, pro-urokinase, urokinase, plasminogen activator, heparin cofactor II, activated protein C (Factor V Leiden), Protein C, antithrombin, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), the product of Wilson's disease gene PWD, Cu/Zn superoxide dismutase, aromatic aminoacid decarboxylase, tyrosine hydroxylase, acetylcholine synthetase, prohormone convertases, protease inhibitors, lactase, lipase, trypsin, gastrointestinal enzymes including chyromotrypsin, and pepsin, adenosine deaminase, α1 anti-trypsin, tissue inhibitor of metalloproteinases (TIMP), GLUT-1, GLUT-2, trehalose phosphate synthase, hexokinases I, II and III, glucokinase, any one or more of the individual chains or types of collagen, elastin, fibronectin, thrombospondin, vitronectin and tenascin, and suicide genes such as thymidine kinase and cytosine deaminase. Other useful proteins include those involved in lysosomal storage disorders, including acid β-glucosidase, α-galactosidase a, α-1-iduronidase, iduroate sulfatase, lysosomal acid α-glucosidase, sphingomyelinase, hexosamina\idase A, hexomimidases A and B, arylsulfatase A, acid lipase, acid ceramidase, galactosylceramidase, α-fucosidase, α-, β-mannosidosis, aspartylglucosaminidase, neuramidase, galactosylceramidase, heparan-N-sulfatase, N-acetyl-α-glucosaminidase, Acetyl-CoA: α-glucosaminide N-acetyltransferase, N-acetylglucosamine-6-sulfate sulfatase, N-acetyl-galactosamine-6-sulfate sulfatase, arylsulfatase B, β-glucuoronidase and hexosaminidases A and B.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other useful proteins include truncated receptors which lack their transmembrane and cytoplasmic domain. These truncated receptors can be used to antagonize the function of their respective ligands by binding to them without concomitant signaling by the receptor. Other types of non-naturally occurring gene sequences include sense and antisense molecules and catalytic nucleic acids, such as ribozymes, which could be used to modulate expression of a gene.

Other useful transgenes include those that encode antigenic peptides capable of generating an immune response. Recombinant vectors comprising these transgenes can be used for genetic immunization. Useful transgenes include those that encode peptides specific for Epstein Barr virus; HIV; simian immunodeficiency virus (SIV); human T-cell leukemia viruses I and II (HTLV-I and HTLV-II); hepatitis A, B, C, D, E and SEN; pseudorabies virus; rabies virus; cytomegalovirus; respiratory syncytial virus; parainfluenza virus types 1–4; mumps virus; rubella virus; polio virus; measles virus; influenza virus types A, B and C; rotavirus; herpes simplex viruses types 1 and 2; varicella-zoster virus; human herpes virus type 6, 7 and 8; hantavirus; denguevirus, sindbisvirus, adenoviruses; *chlamydia pneumoniae; chlamydia trachomatis; mycoplasma pneumoniae; mycobacterium tuberculosis*; atypical mycobacteria; feline leukemia virus; feline immunodeficiency virus; bovine immunodeficiency virus; equine infectious anemia virus; caprine arthritis encephalitis virus; visna virus; *Staphlococcus* species and *Streptococcus* species. The transgenes may also be directed against peptides from tumor antigens to provide immunization for tumors and cancers.

Expression Control Sequences

A great number of expression control sequences—native, constitutive, inducible and/or tissue-specific—are known in the art and may be utilized to drive expression of the transgene and the nucleic acid sequences encoding the replication and encapsidation functions of the rAAV, the helper functions and the ligand. The choice of expression control sequence depends upon the type of expression desired. For eukaryotic cells, expression control sequences typically include a promoter, an enhancer, such as one derived from an immunoglobulin gene, SV40, cytomegalovirus, etc., and a polyadenylation sequence. The polyadenylation sequence generally is inserted following the transgene sequences and before the 3' flanking sequence of the transgene. A transgene-carrying molecule useful in the present invention may also contain an intron, desirably located between the promoter/enhancer sequence and the transgene. One possible intron sequence is also derived from SV40 and is referred to as the late16S/19S intron. Another vector element that may be used is an internal ribosome entry site (IRES), as described above. An IRES element is used to produce more than one polypeptide from a single transcript. An IRES element can be used for the transgene or for any of the other nucleic acid sequences encoding the replication and encapsidation polypeptides, the helper functions or the ligand. Selection of these and other common vector elements are conventional and many such sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer [see, e.g., Boshart et al, *Cell*, 41:521–530 (1985)], the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible metallothionine (MT) promoter; the dexamethasone (Dex)-inducible mouse mammary tumor virus (MMTV) promoter; the T7 polymerase promoter system [WO 98/10088]; the ecdysone insect promoter [No et al, *Proc. Natl. Acad. Sci. USA*, 93:3346–3351 (1996)]; the tetracycline-repressible system [Gossen et al, *Proc. Natl. Acad. Sci. USA*, 89:5547–5551 (1992)]; the tetracycline-inducible system [Gossen et al., *Science*, 268:1766–1769 (1995); see also Harvey et al., *Curr. Opin. Chem. Biol.*, 2:512–518 (1998)]; the RU486-inducible system [Wang et al., *Nat. Biotech.*, 15:239–243 (1997) and Wang et al., *Gene Ther.* 4:432–441 (1997)]; and the rapamycin-inducible system [Magari et al., *J. Clin. Invest.*, 100:2865–2872 (1997); Rivera et al., *Nat. Medicine*, 2:1028–1032 (1996)]. Other types of inducible promoters which may be useful in this context are those which are regulated by a specific physiological state, e.g., temperature, acute phase, or in replicating cells only.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters [see Li et al., *Nat. Biotech.*, 17:241–245 (1999)]. Examples of promoters that are tissue-specific are known for liver [albumin, Miyatake et al. *J. Virol.*, 71:5124–32 (1997); hepatitis B virus core promoter, Sandig et al., *Gene Ther.*, 3:1002–9 (1996); alpha-fetoprotein (AFP), Arbuthnot et al., *Hum. Gene Ther.*, 7:1503–14 (1996)], bone [osteocalcin, Stein et al., *Mol. Biol. Rep.*, 24:185–96 (1997); bone sialoprotein, Chen et al., *J. Bone Miner. Res.*, 11:654–64 (1996)], lymphocytes [CD2, Hansal et al., *J. Immunol.*, 161:1063–8 (1998); immunoglobulin heavy chain; T cell receptor a chain], neuronal [neuron-specific enolase (NSE) promoter, Andersen et al. *Cell. Mol. Neurobiol.* 13:503–15 (1993); neurofilament light-chain gene, Piccioli et al., *Proc. Natl. Acad. Sci. USA*, 88:5611–5 (1991); the neuron-specific vgf gene, Piccioli et al., *Neuron.* 15:373–84 (1995)]; among others.

Of course, not all vectors and expression control sequences will function equally well to express all of the transgenes or other nucleic acid sequences of this invention. However, one of skill in the art may make a selection among these expression control sequences without departing from the scope of this invention. Suitable promoter/enhancer sequences which function in the appropriate host cell of choice may be selected by one of skill in the art using the guidance provided by this application. Such selection is a routine matter and is not a limitation of the molecule or construct.

One may identify a suitable expression control sequence for a desired transgene by selecting one or more expression control sequences and operably linking the expression control sequence to the nucleic acid sequence to be regulated. Then, one may insert these operably linked sequences comprising the expression control sequence and regulated sequence into the genome of the adenovirus vector. In one embodiment, one may insert a recombinant viral genome comprising the expression control sequence and the transgene into a vector of the instant invention. After following one of the methods for producing and packaging the rAAV as taught in this specification one may infect suitable cells in vitro or in vivo. The number of copies of the transgene in the cell may be monitored by Southern blotting or quantitative PCR; the level of RNA expression may be monitored by Northern blotting or quantitative RT-PCR; and the level of protein expression may be monitored by Western blotting, immunohistochemistry, ELISA, RIA, tests of the transgene's gene product's biological activity, either in vitro or in vivo, or tests for correction or amelioration of a genetic defect.

Flanking Elements

The naturally-occurring AAV ITRs consist of repeated sequences, usually but not necessarily approximately 145 nucleotides in length, at the 5' and 3' ends of the AAV genome. The AAV ITRs are required for replication, excision and encapsidation of both wild type and recombinant AAV virions. The ITRs flank the transgene when the AAV DNA integrates into a host cell chromosome. When rAAV is rescued from the host chromosome, the ITRs excise along with the transgene and remain in flanking positions surrounding the rescued DNA, in a form suitable for packaging into virions. The ITRs may be derived from any one of the adeno-associated viruses known, including AAV serotypes 1 to 6. In a preferred embodiment of the invention, the rAAV comprises a selected transgene operably linked to expression regulatory sequences and AAV flanking elements.

Host Cells

Any type of mammalian cell that can be adapted to cell culture may be used as a host cell to produce the recombinant viral genome. In general, a host cell used in this invention is one that may be infected by the adenovirus vector of the instant invention. Another preferred characteristic of the host cell is that it is able to replicate the rAAV at high levels.

Appropriate host cells include, without limitation, CHO, BHK, MDCK and various murine cells, e.g., 10T1/2 and WEHI cells, African green monkey cells such as VERO, COS 1, COS 7, BSC 1, BSC 40, and BMT 10, and human cells such as WI38, MRC5, A549, human embryonic retinoblast (HER), human embryonic kidney (HEK), human embryonic lung (HEL) and HT1080 cells. In a preferred embodiment, appropriate cells include 293 cells (human embryonic kidney cells that express adenoviral E1a and E1b proteins), 911 or PER.C6 cells (human embryonic retinoblast cells that express adenoviral E1; see WO 97/00326), B50 cells (HeLa cells that express AAV rep and cap, see PCT US98/19463), 84-31 cells (293-based cells that express adenovirus E1a, E1b and E4, Ref. 4), 10-3 cells (293-based cells that express adenovirus E1a, E1b and E4ORF6, Ref. 11), 3T3 cells (mouse embryonic fibroblast cell line), NIH3T3 cells (subline of 3T3 cells), HepG2 cells (human liver carcinoma cell line), Saos-2 cells (human osteogenic sarcoma cell line), HuH7 cells or HeLa cells (human carcinoma cell line).

In addition to the host cells listed above, other host cells may be used. One may determine whether a cell line would be suited for use as a mammalian host cell by infecting the cell line with an adenovirus of the instant invention in the presence of rep, cap and all required helper functions, culturing the cells under conditions in which rAAV is produced, and then measuring the titer of infectious rAAV. One may then compare the titer of infectious rAAV produced in the potential host cell with the titers produced by other host cells to determine whether the cell line is good for rAAV production.

Methods of Producing Recombinant Adeno-Associated Virus from Adenovirus

Another aspect of the instant invention is a method of producing rAAV from the adenovirus of the instant invention. The method comprises the steps of:

1. Infecting host cells comprising an rAAV genome with an adenovirus comprising a rep gene under the regulatory control of a minimal promoter or no promoter;

2. growing the infected host cells under conditions in which the rAAV genome is excised, replicated and encapsidated; and 3. collecting the rAAV from the mammalian host cells.

The host cells may be any mammalian cell known in the art or as described herein. The host cell, prior to infection by the adenovirus comprising the rep gene, may be one that expresses one or more of the following genetic elements: 1) the cap gene, 2) some or all necessary helper functions (e.g., 293 cells), and/or 3) an rAAV genome. Alternatively, the host cell may comprise none of these genetic elements prior to infection by the adenovirus. In this case, the genetic elements are supplied by the adenovirus comprising the rep gene, other viral vectors, and/or plasmids.

The host cells may be infected by the adenovirus by any method known in the art or as described herein. Methods for infecting host cells with adenoviruses are well known in the art and are also described herein. Once the host cell has been infected, the helper functions are activated and rep and cap are produced. Low levels of Rep78 and Rep68 are produced because the p5 promoter has been replaced by a minimal promoter or by no promoter. This, combined with levels of Rep52 and Rep40, both expressed from the adenoviral p19 promoter, and the capsid proteins, expressed from the AAV p40 promoter, are sufficient to produce high titers of rAAV.

Methods of producing rAAV using other viral vectors in which Rep interferes with viral replication also may be performed following the teachings of the instant specification.

The rAAV may be purified from the supernatant produced by the host cells or from cell lysates by any method known in the art or as described herein. A method of collecting and purifying rAAV is described in Examples 5 and 6.

The method is easily scaled to industrial production because it does not require transfection of a large number of host cells to produce rAAV. In a preferred embodiment, only a single infection of host cells by an adenovirus is required to produce rAAV in large amounts at high titers. See, e.g., Example 5. In another preferred embodiment, host cells are co-infected with two different adenoviruses, one comprising rep downstream of a minimal promoter or no promoter and cap, and the other adenovirus comprising the rAAV genome. Infection of host cells by adenovirus is highly efficient and may be easily scaled to a large number of cells.

The instantly described method produces rAAV at a high titer. In a preferred embodiment, the titer is at least $10^2$ particles per cell; preferably at least $10^3$ particles per cell; more preferably at least $10^4$ particles per cell; and, even more preferably, at least $10^5$ or $10^6$ particles per cell. The instant invention also encompasses lysates and supernatants of host cells comprising rAAV. These lysates and supernatants differ from those produced by prior art methods because of the higher level of rAAV contained therein without concentration.

rAAV Compositions

The rAAV produced by the method of this invention may be formulated as a pharmaceutical or pharmacological composition for use for any form of transient and stable gene transfer in vivo and in vitro. The composition comprises at least the rAAV and a pharmaceutically acceptable carrier. The rAAV may be used for in vivo and ex vivo gene therapy, genetic immunization, in vitro protein production and diagnostic assays.

For gene therapy, the rAAV may be introduced into cells ex vivo or in vivo. Where the virus is introduced into a cell ex vivo, the rAAV may be used to infect a cell in vitro, and then the cell may subsequently be introduced into a mammal (e.g., into the portal vein or into the spleen), if desired. Alternatively, the rAAV may be administered to a mammal directly, e.g., intravenously or intraperitoneally. A slow-release device, such as an implantable pump, may be used to facilitate delivery of the virus to a cell. Where the virus is administered to a mammal, the specific cells to be infected may be targeted by controlling the method of delivery. For example, intravascular administration of rAAV to the portal vein or to the hepatic artery may be used to facilitate targeting rAAV to a liver cell.

The rAAV produced by the above-described method may be administered to a patient, preferably suspended in a biologically compatible solution or pharmaceutically acceptable delivery vehicle. A suitable vehicle includes sterile saline. Other aqueous and non-aqueous sterile suspensions known to be pharmaceutically acceptable carrier and well known to those of skill in the art may be employed for this purpose.

The rAAV is administered in sufficient amounts to infect the desired cells and provide sufficient levels of transduction and expression of the selected transgene (or viral gene products in the case of a vaccine) to provide some level of a corrective effect without undue adverse or with medically acceptable physiological effects, which can be determined by those skilled in the medical arts. Conventional and pharmaceutically acceptable routes of administration include direct administration to the target organ, tissue or site; intranasal; intravenous; intramuscular; subcutaneous; intradermal; oral and other parenteral routes of administration. Routes of administration may be combined, if desired.

Dosages of rAAV will depend primarily on factors such as the condition being treated and the selected gene. The dosage may also vary depending upon the age, weight and health of the patient. For example, an effective human dosage of rAAV is generally in the range of from about 0.5 ml to 50 ml of saline solution containing rAAV at concentrations of $1\times10^7$ or $1\times10^8$ or $1\times10^9$ or $1\times10^{10}$ or $1\times10^{11}$ or $1\times10^{12}$ or $1\times10^{13}$ or $1\times10^{14}$ or $1\times10^{15}$ or $1\times10^{16}$ particles per dose administered. The dosage will be adjusted to balance the corrective benefits against any adverse side effects. The levels of expression of the selected gene may be monitored to determine the type and frequency of dosage administration.

The following examples of the present inventions are illustrative only, and are not intended to limit the scope of the invention.

EXAMPLE 1

Cell Lines and Viruses and Maintenance and Propagation Thereof

All cell lines are maintained in Dulbecco's Modified Eagle's Medium (DMEM; Gibco BRL) supplemented with 10% FBS (Hyclone) and 50 µg/ml of penicillin, 50 µg/ml of streptomycin, and 10 µg/ml of neomycin (Gibco BRL). Human embryonic kidney cell line 293 is obtained from ATCC(CRL 1573). 293-derived 84-31 cells (1) which express adenovirus E1/E4orf6 proteins, and HeLa-derived B50 cells (7) which express AAV-2 Rep and Cap proteins from the native p5 promoter, are obtained from Dr. Guangping Gao, Institute for Human Gene Therapy, University of Pennsylvania. 293-CG3 is a 293-derived cell line carrying stably integrated copies of AAV ITRs flanking GFP as marker gene (Chen et al., unpublished data). Human adenovirus type 5 (ATCC VR-5) and derived recombinant adenoviruses are propagated on 293 cells and purified through CsCl gradient centrifugation according to the method of Jones and Shenk with modification (2).

EXAMPLE 2

Construction of Plasmids and Generation of Recombinant Adenoviruses

Figure 2:
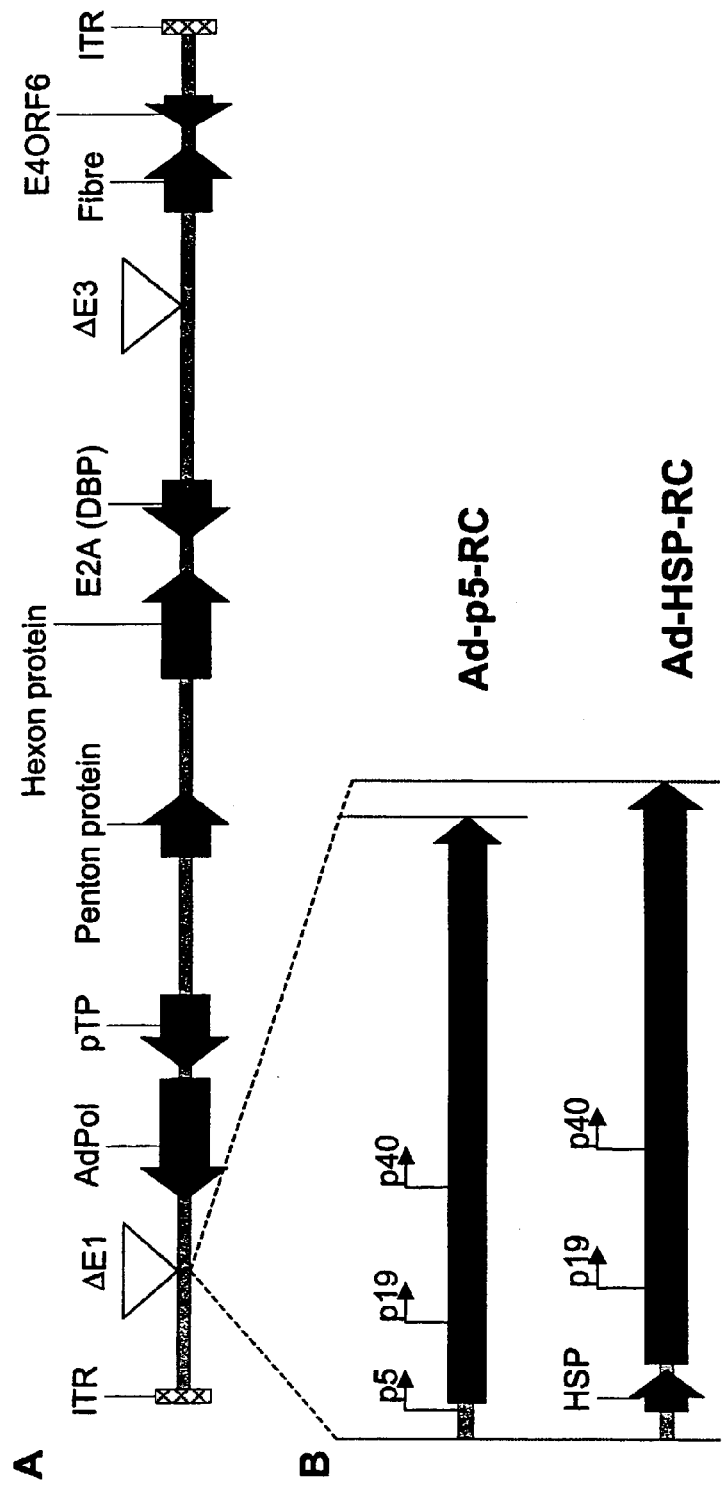
FIG. 2A. Genome of the parental E1/E3 deleted adenovirus.
FIG. 2B. Schematic diagrams of the recombinant adenoviruses Ad-p5-RC and Ad-HSP-RC showing insertion of p5-rep-cap or HSP-rep-cap DNA sequences into the E1 locus of the parental viral genome to generate Ad-p5-RC or Ad-HSP-RC, respectively.

Standard recombinant DNA techniques are employed to create recombinant plasmids (3). DNA containing the rep and cap sequences of pAV2 (ATCC 37216) between DraIII site (nucleotide 241, upstream of the AAV-2 p5 promoter) and NcoI site (nucleotide 4489, downstream of the polyA signal) is removed and replaced through multiple cloning steps with a DNA cassette containing GFP under the transcriptional control of elongation factor 1 alpha (EF1α) promoter and upstream of the SV40 polyA signal to create pAV2cisEFGFP (FIG. 1). The AAV-2 rep and cap genes located between a Dra III site (nucleotide 241, upstream of the p5 promoter) and a BsaI site (nucleotide 4464, downstream of the polyA signal) are further subcloned to obtain pAd-p5-RC (FIG. 1). A small DNA fragment between nucleotides 241 and 287 of pAd-p5-RC containing the p5 promoter is removed and replaced with a *Drosophila melanogaster* minimal heat shock protein (HSP) promoter from pIND (Invitrogen) to create pAd-HSP-RC (FIG. 1). Recombinant adenoviruses Ad-p5-RC and Ad-HSP-RC (FIG. 2) are generated according to standard protocols known in the art (see, e.g., Refs. 4 and 12). The recombinant adenoviruses are passaged five to six times on appropriate mammalian cells to generate a stock of recombinant adenovirus that is used for production of rAAV.

EXAMPLE 3

Transfection of 293 Cells and Selection of the 293-CG3 Stable Cell Line 293 cells are grown to ~70% confluency in 6-cm tissue culture dishes and co-transfected overnight with 1 µg pIRESIneo and 10 µg pAV2cisEFGFP by the calcium phosphate transfection method. The monolayer is replenished with fresh medium containing 10% FBS and cultured for 24 hours. Following trypsinization, cells are seeded at a 1:20 dilution in fresh medium containing 10% FBS. After incubation for another 24 hours, fresh medium containing 1,250 µg/ml of G418 (Gibco BRL) is added to the cell monolayer for genetic selection of G418-resistant cells. The medium containing G418 is replaced every 3–4 days to allow formation of G418-resistant cell colonies. A total of fifty colonies are picked, six of which demonstrate constitutive GFP expression. These six clones are expanded and tested for their ability to rescue functional rAAV by transfection with pBV-EiOV-RC, a plasmid that carries adenovirus E2A, E4ORF6, and VAI genes as well as AAV rep-cap genes. One cell clone, 293-CG3, shows high efficiency of rAAV rescue and is expanded and used for further experiments.

EXAMPLE 4

PCR Analysis of AAV-2 Rep and Cap Genes Inserted into the Adenovirus Genome

In order to determine the integrity of AAV-2 rep and cap genes recombined into the adenovirus genome, a polymerase chain reaction (PCR) assay is employed. Four sets of primer pairs overlapping the entire DNA sequence encoding AAV-2 rep and cap genes, as well as the junctions between adenoviral and rep-cap sequences, are synthesized. These primers are:

HC#30 (5'-CGTAACCGAGTAAGATTTGG-3'; SEQ ID NO: 1),

HC#31 (5'-ATGTTGGTGTTGGAGGTGAC-3'; SEQ ID NO: 2),

HC#32 (5'-TGGACCAGAAATGCAAGTCC-3'; SEQ ID NO: 3),

HC#33 (5'-AGCCTTGACTGCGTGGTGGT-3'; SEQ ID NO: 4),

HC#34 (5'-GTACCTGTATTACTTGAGCA-3'; SEQ ID NO: 5),

HC#35 (5'-ACGAGTCAG GTATCTGGTGC-3'; SEQ ID NO: 6),

HC#36 (5'-GGACTTTACTGTGGACACTA-3'; SEQ ID NO: 7), and

HC#37 (5'-GACCCAGACTACGCTGACGA-3'; SEQ ID NO: 8).

To obtain adenoviral DNA for the PCR assay, a miniprep method is employed. Briefly, 293 cells are grown in 10-cm dishes until nearly confluent and then infected with either Ad-HSP-RC or Ad-p5-RC for 3 days. Infected cells are harvested, pelleted and lysed in DOC lysis buffer (100 mM Tris-HCl, pH9.0, 20% ethanol, 0.4% sodium deoxycholate). Cellular nucleic acids are precipitated by spermine-HCl and supernatant is collected. The supernatant is then treated with RNase A and pronase, followed by extraction with phenol-chloroform. Adenoviral DNA in the supernatant is precipitated with isopropanol and dissolved in TE/RNase buffer (10 mM Tris-HCl, pH8.0, 1 mM EDTA, 20 µg/ml RNase).

Figure 3:
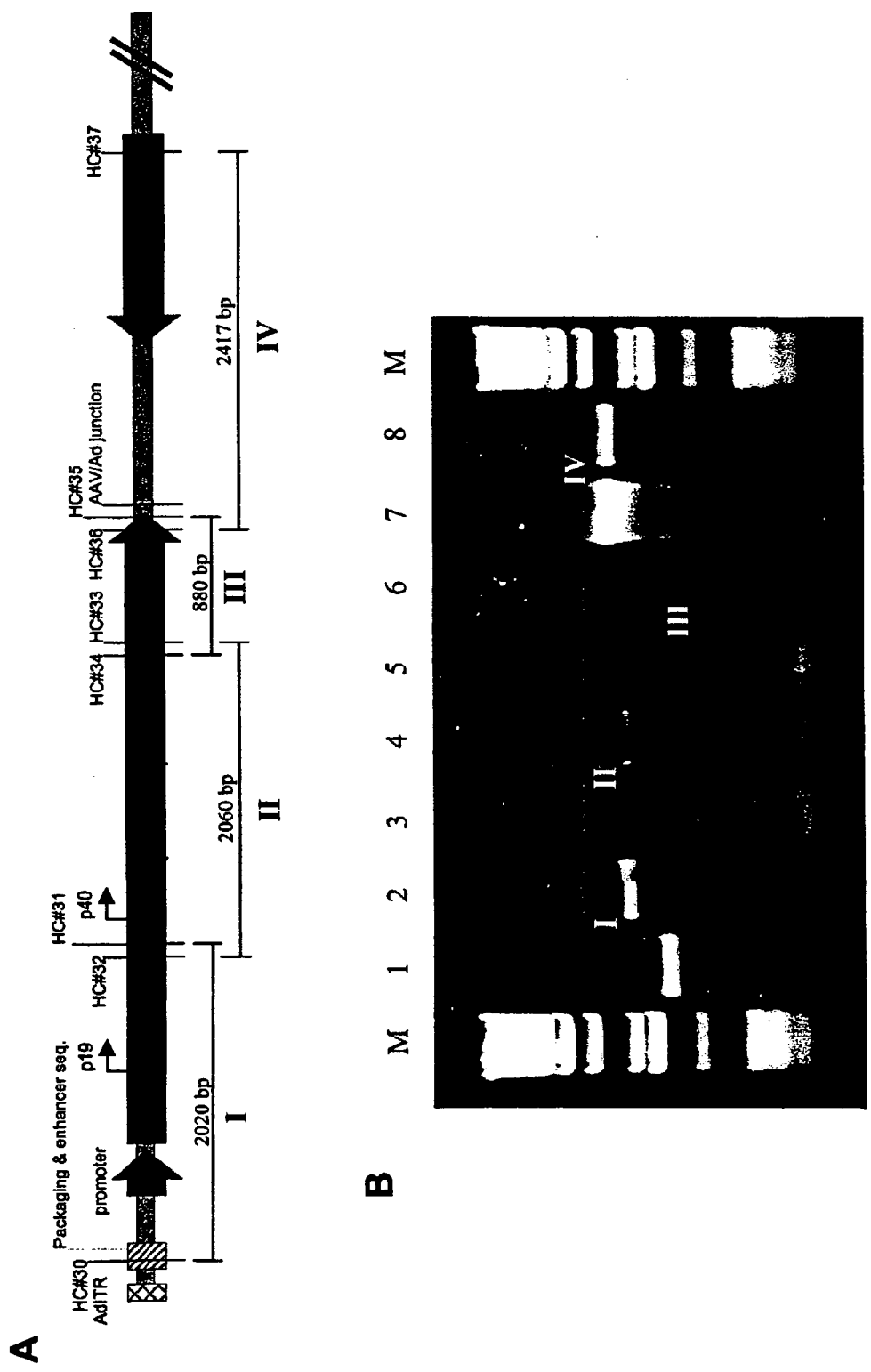
FIG. 3A. Schematic diagram of the rep-cap insert in the E1 locus of Ad-p5-RC or Ad-HSP-RC showing the location of PCR primers relative to the viral genome and expected PCR DNA products I, II, III, and IV. PCR analysis is used to determine the integrity of AAV rep-cap DNA sequences inserted into the adenovirus genome.
FIG. 3B. Ethidium bromide stained agarose gel of PCR products using primers whose locations are shown in FIG. 3A. Lanes 1, 3, 5, 7 are PCR products from viral DNA of Ad-p5-RC. Lanes 2, 4, 6, 8 are PCR products from viral DNA of Ad-HSP-RC. M, 1 kb DNA ladder size marker (Gibco BRL).

The PCR assay is performed using the Robocycler Gradient 96 thermal cycler (Stratagene), PCR products are separated on a 1% agarose gel and DNA is stained with ethidium bromide. As shown in FIG. 3, all four expected DNA PCR products are obtained when using Ad-HSP-RC DNA as template, indicating that the full-length AAV-2 rep-cap DNA is present in the genome of this recombinant. However, the 880 bp PCR product III is not amplified from Ad-p5-RC DNA, suggesting a rearrangement or deletion event in rep-cap DNA sequences of this recombinant. These results indicate the integrity and stability of HSP-rep-cap DNA after insertion into the E1 locus of the adenoviral genome, and point out that p5-rep-cap DNA sequences inserted into the same locus are unstable.

EXAMPLE 5

Production of rAAV Through Infection of 293-CG3 Cells with Ad-HSP-RC

Since Ad-HSP-RC is shown to contain full length AAV-2 rep-cap DNA sequences, its utility to produce rAAV is analyzed. 293-CG3 cells are seeded in 6-well plates at a density of $1.0 \times 10^6$ cells/well. Twelve to fifteen hours later, the culture media is removed from the cell monolayer and dilutions of Ad-HSP-RC virus in 0.5 ml of serum-free DMEM are added to the cells. Following a 30 min. incubation, an additional 2.5 ml of DMEM containing 10% FBS is added and the infection is allowed to proceed for a total of 3 days. Infected cells are harvested and pelleted. Cell pellets are lysed in 1 ml of lysis buffer (50 mM Tris-HCl, pH7.4, 1.0 mM $MgCl_2$, 0.5% DOC) with sonication for 3×1 min. Cell debris is removed by centrifugation at 3,000 rpm using a Beckman GS-6R centrifuge for 10 min. The lysate supernatant is collected for titration of rAAV.

To titrate the rAAV in the lysate, 84-31 cells (1) are plated 3–4 hours before use on 24-well plates at a density of $2 \times 10^5$ cells/well. The rAAV lysate is diluted in DMEM containing 10% FBS and heated at 56° C. for 60 min to inactivate contaminating Ad-HSP-RC. The rAAV lysate is added to the monolayer, cells are incubated for approximately 24 hours, and GFP-expressing cells are scored as transducing units (TU).

Figure 4:
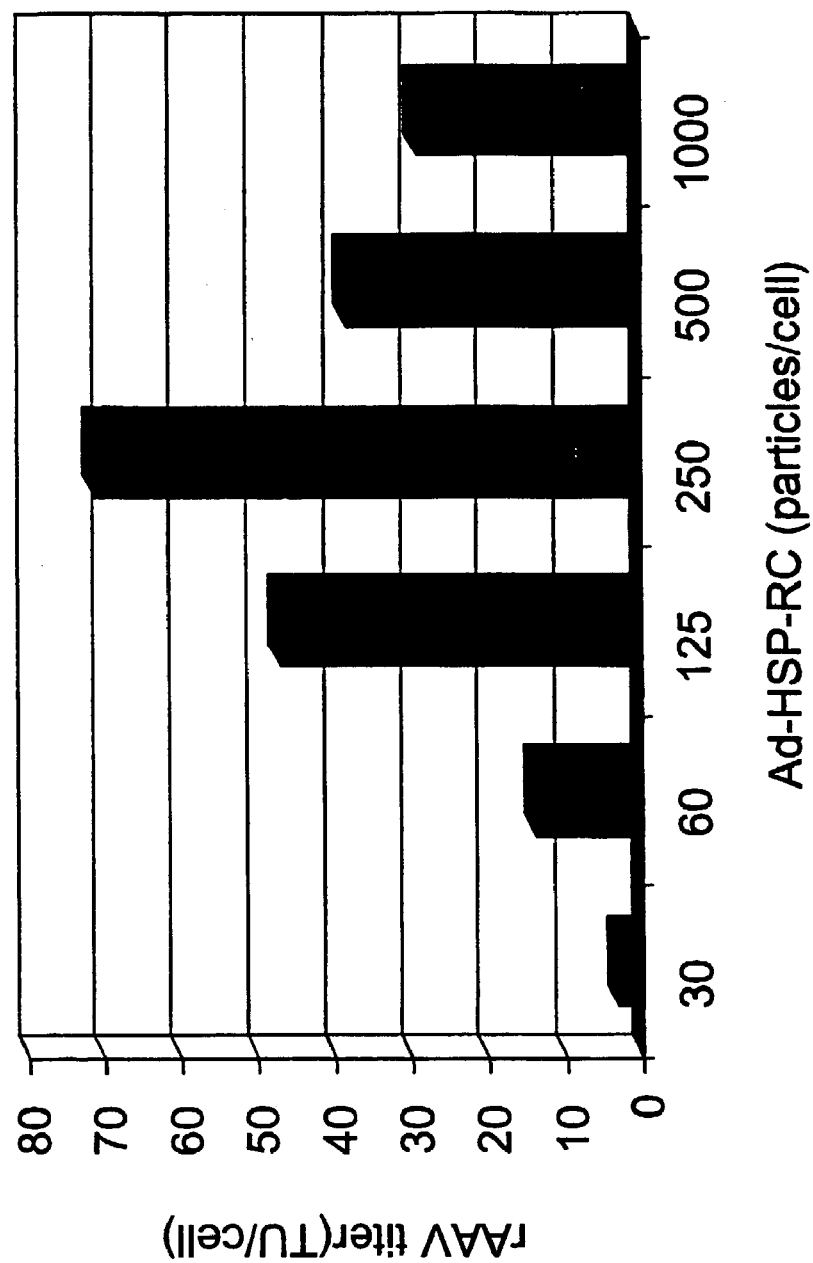
FIG. 4. Production of rAAV after infection of 293-CG3 cells with Ad-HSP-RC.

As shown in FIG. 4, the results demonstrate that rAAV is successfully produced through infection of 293-CG3 cells with the recombinant Ad-HSP-RC. The rAAV titer increases by increasing the multiplicity of infection (MOI) of Ad-HSP-RC. Using an MOI of 250 particles/cell, as much as 70 TU/cell of rAAV is produced. However, further increasing the MOI of the Ad-HSP-RC virus does not increase the yield of rAAV. Instead, a slight decrease in rAAV yield is observed, probably due to the increased cytotoxicity associated with higher MOI of Ad-HSP-RC virus.

EXAMPLE 6

Production of rAAV Through Co-Infection of 293 Cells with Ad-HSP-RC and Ad-AAV-LacZ In the previous example, AAV vector sequences are stably integrated into the host cell chromosome while rep-cap functions necessary for their rescue and packaging into rAAV are provided by Ad-HSP-RC. As a separate measure to determine the functionality of the Ad-HSP-RC recombinant, AAV vector sequences are delivered exogenously into 293 cells to determine whether they could be rescued and packaged into rAAV particles following infection with Ad-HSP-RC. To perform this experiment, 293 cells are seeded on 6-well plates at a density of $1 \times 10^6$ cells/well. 12–15 hours later, the cells are co-infected with Ad-HSP-RC and Ad-AAV-LacZ, an E1-deleted adenovirus containing the *E. coli* lacZ gene flanked by AAV-2 ITR's inserted into the E1 locus (4).

Figure 5:
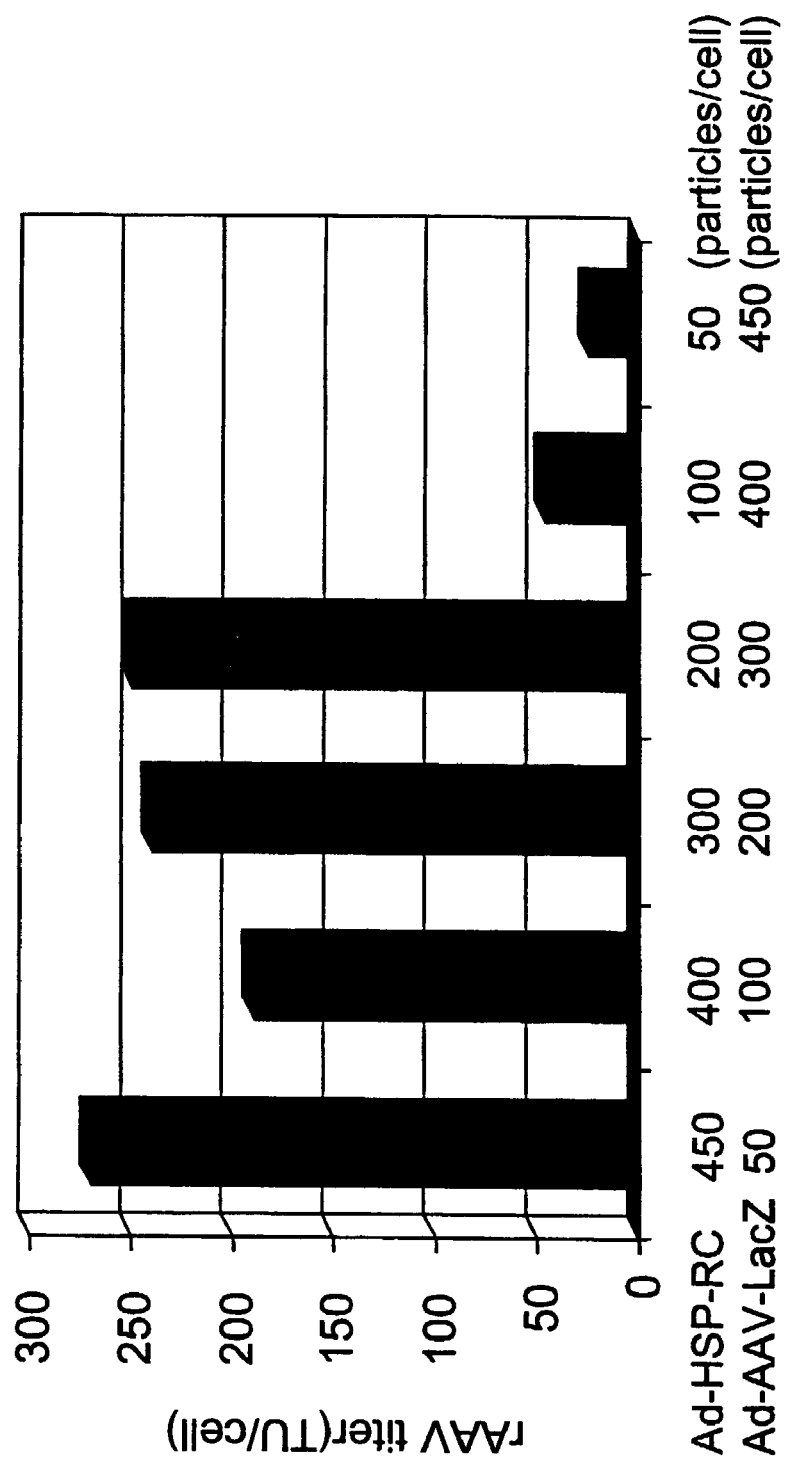
FIG. 5. Production of rAAV after co-infection of 293 cells with Ad-HSP-RC and Ad-AAV-LacZ.

To further investigate the effects of varying MOI's of either virus on rAAV yield, the following experiment is performed. Different quantities of the two viruses (50 to 450 particles/cell) are mixed together, keeping the total inoculum at a constant 500 particles/cell (FIG. 5). The virus mixture is diluted in 0.5 ml of serum-free DMEM at various particle/cell ratios (50:450, 100:400, 200:300, 300:200, 400:100, and 450:50) and is added to the cell monolayer. Thirty minutes later, an additional 2.5 ml of DMEM containing 10% FBS is added and the cells are incubated in the presence of virus inoculum for 3 additional days.

Infected cells are harvested, lysed, and rAAV titrated as described in Example 5 except that rAAV transduction is scored cells by X-gal staining according to standard protocols (5). Cell stain is possible because the rAAV in this experiment carries lacZ as a transgene. Briefly, the rAAV transduced cells are first fixed with 0.5 ml of 0.05% glutaraldehyde for 10 min and then rinsed with 3×0.5 ml of PBS.

Fixed cells are stained with 0.5 ml of X-gal solution at room temperature overnight. The X-gal solution is removed, 0.5 ml of 70% ethanol is added to terminate the reaction, and blue-staining cells are scored as transducing units.

As shown in FIG. 5, the results clearly demonstrate that co-infection of 293 cells by the two recombinant adenoviruses, Ad-HSP-RC and Ad-AAV-LacZ, can produce high titers of rAAV in 293 cells. The data indicate that with decreasing MOI of Ad-HSP-RC and increasing MOI of Ad-AAV-LacZ, the yield of rAAV produced remains relatively steady until the Ad-HSP-RC MOI reaches 100 particles/cell or less. Further decrease of the MOI of Ad-HSP-RC dramatically decreases the rAAV yield, presumably due low levels of Rep and Cap proteins that are produced at the lower MOI's. On the other hand, increasing the MOI of Ad-AAV-LacZ does not increase the rAAV yield. While the conventional method for rAAV production using plasmid co-transfection is limited in its yield of rAAV, the current invention provides the means to easily and efficiently produce high yields of rAAV.

EXAMPLE 7

Time-Course and Particle Ratio Studies of rAAV Production Through Co-Infection of 293 Cells with Ad-HSP-RC and Ad-AAV-LacZ To further study the conditions required for optimal production of rAAV through co-infection of 293 cells with Ad-HSP-RC and Ad-AAV-LacZ, separate time-course and MOI studies are performed. 293 cells are seeded in 6-well plates as described in Example 6 and are infected with both viruses for different time intervals or at different particles/cell ratios. Infected cells are harvested and lysed, and rAAV is titrated as described in Example 6. For the time-course study, 100 particles/cell each of Ad-HSP-RC and Ad-AAV-LacZ are used to infect 293 cells for various times.

Figure 6:
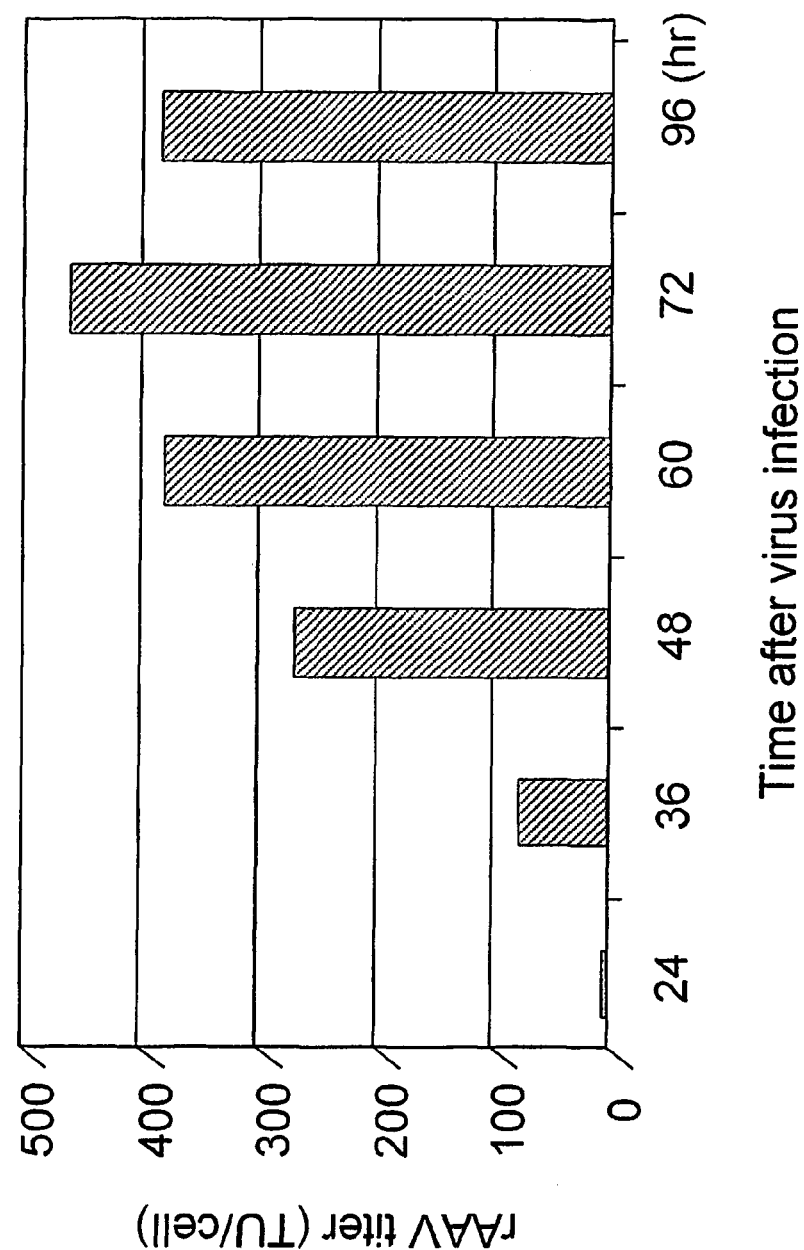
FIG. 6. Time-course study of rAAV production after co-infection of 293 cells with Ad-HSP-RC and Ad-AAV-LacZ.
Figure 7:
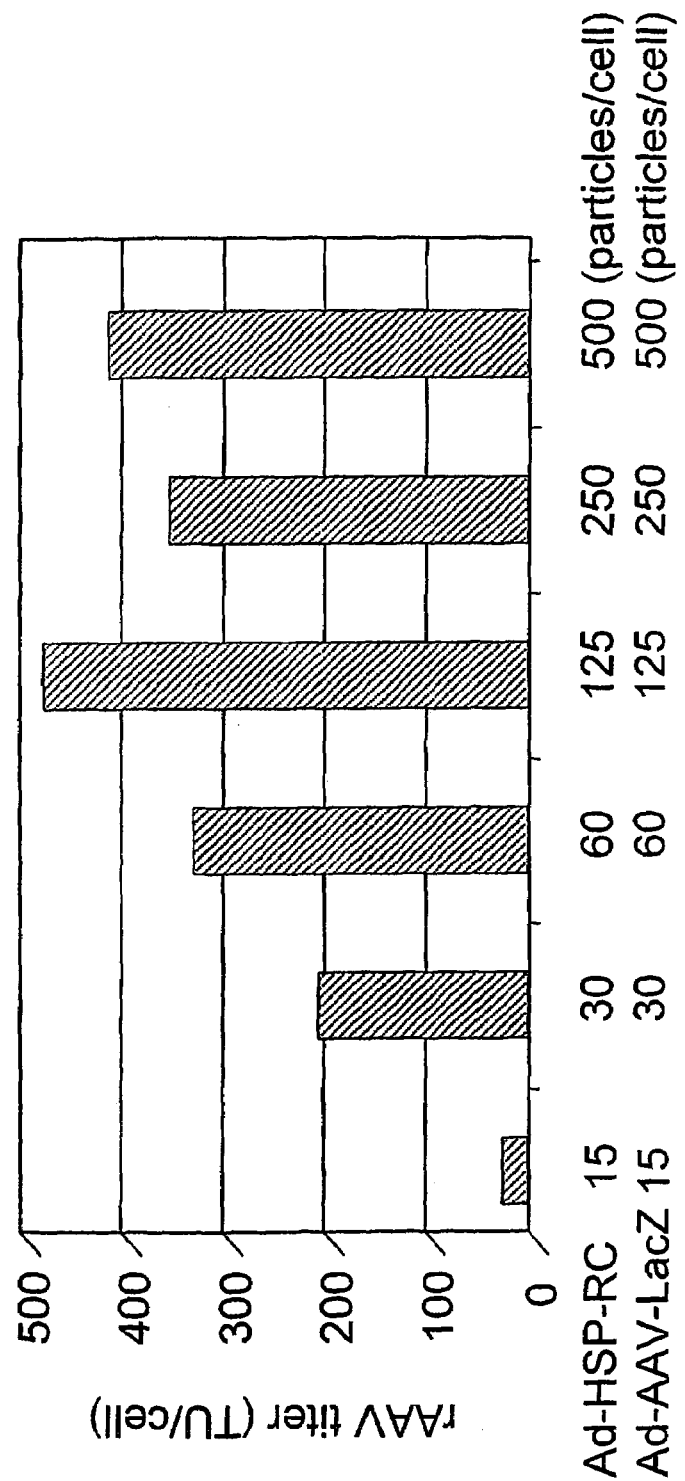
FIG. 7. Multiplicity of infection study of rAAV production after co-infection of 293 cells with Ad-HSP-RC and Ad-AAV-LacZ.

As shown in FIG. 6, the results demonstrate that rAAV is detected as early as 24 hours post-infection by the two viruses, but its levels peaks at 72 hours after infection. More than 200 TU/cell of rAAV is produced between 48 and 96 hours after infection by the two viruses. To determine the optimal MOI of the two viruses required for high level rAAV production, 293 cells are infected by the two viruses at equal MOI's for 72 hours and harvested and rAAV titers are determined. As shown in FIG. 7, it is apparent that with increasing input of Ad-HSP-RC and Ad-AAV-LacZ viruses, the yield of rAAV increases up to an MOI of 125 particles/cell of each virus. Further increasing the input adenovirus MOI does not increase the rAAV yield and instead results in a slight decrease of rAAV yield. This may be due to higher cytopathic effects resulting from higher MOI's of input adenovirus which in turn may affect rAAV yields from the infected cell.

EXAMPLE 8

Analysis of rAAV DNA Replication Following Co-Infection of 293 Cells with Ad-HSP-RC and Ad-AAV-LacZ To analyze the excision and replication of rAAV DNA from the Ad-AAV-LacZ hybrid genome, extrachromosomal DNA is analyzed in 293 cells co-infected by Ad-HSP-RC and Ad-AAV-LacZ using the method of Hirt (6). As a positive control for rAAV DNA rescue and replication, a separate system previously shown to produce rAAV at high titers is similarly assayed in parallel. The control system is based on the use of the B50 cell line, that was previously created by stably transfecting into HeLa cells a rep/cap-containing plasmid utilizing endogenous AAV-2 promoters (7). rAAV production in this cell line occurs in a two-step process: B50 cells are initially infected with sub100r, an adenovirus temperature-sensitive mutant in the E2b gene, to induce rep and cap expression and provide helper functions. 24 h later, cell are infected by a hybrid E1-deleted adenovirus in which the AAV vector sequence is cloned in the E1 region of a replication-defective adenovirus. In the presence of Rep and Cap proteins expressed by the cell, as well as adenoviral helper functions expressed from sub 100r, the rAAV genome delivered by the hybrid vector is rescued, replicated and encapsidated into rAAV particles (7).

293 cells are grown in 10-cm dishes to subconfluency and are either co-infected with Ad-HSP-RC plus Ad-AAV-LacZ or with Ad-p5-RC plus Ad-AAV-LacZ at 200 particles/cell of each virus. Positive control B50/sub100r experiments are carried out in a similar fashion except that Ad-AAV-LacZ is added to B50 cells 24 hours after addition of sub 100r, each at 1,000 particles/cell. Negative controls include single virus infections of 293 cells with either Ad-p5-RC, Ad-HSP-RC or Ad-AAV-LacZ alone. Infected cells are harvested 72 hours post-infection and lysed in 0.85 ml of Hirt solution (10 mM Tris-HCl, pH 7.4, 100 mM EDTA, 0.6% SDS). The lysate is mixed with 0.25 ml of 5 M NaCl and incubated at 4° C. overnight. After centrifugation at 14,000 RPM for 40 min. in a Sorvall centrifuge, supernatant is collected and extracted three times with phenol-chloroform. The low molecular weight DNA is precipitated by isopropanol, dissolved in TE/RNase buffer, fractionated by electrophoresis on a 0.8% agarose gel and stained with ethidium bromide.

The results of this experiment are presented in FIG. 8. Co-infection of 293 cells by Ad-HSP-RC and Ad-AAV-LacZ results in the generation of DNA bands of 4.8 and 9.6 kb which correspond to monomeric and dimeric forms of replicating, double-stranded rAAV DNA (FIG. 8, lane 4). The positive control also shows the same two DNA species following infection of B-50 cells with sub100r and Ad-AAV-LacZ (FIG. 8, lane 6). Neither DNA band is observed in negative controls in which 293 cells are infected singly with either Ad-p5-RC (FIG. 8, lane 1), Ad-HSP-RC (FIG. 8, lane 2), or Ad-AAV-LacZ (FIG. 8, lane 3). Furthermore, co-infection of 293 cells by Ad-p5-RC and Ad-AAV-LacZ also does not result in the formation of either rAAV DNA species (FIG. 8, lane 5), suggesting that Ad-p5-RC is defective in its rep/cap functions for rescue or replication of rAAV DNA.

To confirm that the 4.8 and 9.6 kb extrachromosomal DNA species detected in FIG. 8 does indeed contain the lacZ transgene, and to confirm that low quantities of such DNA species are indeed absent in negative control lanes, a Southern blot analysis is performed. Hirt-extracted DNA, isolated from either 293 cells co-infected by Ad-HSP-RC and Ad-AAV-LacZ or B50 cells infected by sub 100r and Ad-AAV-LacZ, is separated on a 0.8% agarose gel (FIG. 9A). The gel is transferred to a nitrocellulose membrane and hybridized with a digoxigenin labeled, lacZ DNA probe using the DIG High Prime DNA Labeling Detection Starter Kit II from Boehringer Mannheim (FIG. 9B). A lacZ DNA fragment, isolated from a bacterial plasmid, is used as positive control for the Southern blot (FIGS. 9A and 9B, lane 1).

Both monomeric and dimeric forms of replicating rAAV DNA, isolated from either 293 cells co-infected by Ad-HSP-RC and Ad-AAV-LacZ (FIGS. 9A and 9B, lane 5) or B50 cells infected by sub100r and Ad-AAV-LacZ (FIG. 9A and 9B, lane 7), hybridize to the lacZ probe. Southern blotting does not detect any replicated rAAV DNA species following co-infection of 293 cells by Ad-p5-RC and Ad-AAV-LacZ (FIGS. 9A and 9B, lane 6), or from the negative controls which include Hirt DNA from 293 cells infected singly by either Ad-HSP-RC (FIGS. 9A and 9B, lane 2), Ad-p5-RC (FIGS. 9A and 9B, lane 3), or Ad-AAV LacZ (FIGS. 9A and 9B, lane 4). Taken together, these results indicate that co-infection of 293 cells by Ad-HSP-RC and Ad-AAV-LacZ results in rescue and replication of rAAV DNA from the Ad-AAV-LacZ genome, and that replicating rAAV DNA indeed contains the lacZ transgene. Moreover, the lack of replicating rAAV DNA after co-infection of 293 cells by Ad-p5-RC and Ad-AAV-LacZ supports earlier observations that Ad-p5-RC is indeed defective in its rep/cap functions for rescue or replication of rAAV DNA.

EXAMPLE 9

Analysis of Rep/Cap Protein Expression in 293 Cells Infected with Ad-HSP-RC Virus To analyze the expression of Rep and Cap proteins in cells infected by Ad-HSP-RC virus, Western blotting is performed. 293 cells are grown in 10-cm plates to subconfluency and are either infected with Ad-HSP-RC, Ad-AAV-LacZ, or Ad-p5-RC using 200 particles/cell of each virus. 72 hours post-infection, cells are harvested, pelleted, and processed as described by Xiao et al. (8). Briefly, the infected cell pellet from one 10-cm dish is lysed in 0.5 ml lysis buffer containing 10 mM Tris-HCl, pH 8.2, 1% Triton X-100, 1% SDS and 150 mM NaCl by sonication. Samples are separated by SDS-polyacrylamide gel electrophoresis (PAGE) on a 4%~20% gradient polyacrylamide gel and transferred to a nitrocellulose membrane. The Rep proteins are detected using monoclonal antibody 303.9 and Cap proteins are detected using monoclonal antibody B1 (American Research Products, Inc.), both at a 1:20 dilution. Protein-antibody complexes are visualized using the ECL™ Western Blotting Analysis System (Amersham).

As shown in FIG. 10, Rep and Cap proteins are expressed in 293 cells infected with Ad-HSP-RC alone (Lane 3), or co-infected with Ad-HSP-RC and Ad-AAV-LacZ (Lane 5), but not in 293 cells infected with Ad-p5-RC alone (Lane 1), Ad-p5-RC plus Ad-AAV-LacZ (Lane 2), or Ad-AAV-LacZ (Lane 4). Levels of Rep52 and Rep40 proteins expressed following Ad-HSP-RC infection are much higher than those of Rep78 and Rep68, a phenomenon that has been previously reported to contribute to higher levels of rAAV produced (9). The low basal transcriptional activity of the HSP promoter may indeed play an important role in the success of creating the Ad-HSP-RC recombinant adenovirus since it is known that expression of AAV Rep proteins may interfere with adenovirus replication (10). Low level expression of these proteins may minimize the interference but provide enough Rep function for excision and replication of the rAAV genome.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Fisher K J, Gao G P, Weitzman M D, DeMatteo R, Burda J F, Wilson J M. 1996. Transduction with recombinant adeno-associated virus for gene therapy is limited by leading-strand synthesis. J. Virol. 70(1):520–532.
2. Jones N, Shenk T. 1978. Isolation of deletion and substitution mutants of adenovirus type 5. Cell 13(1):181–188.
3. Sambrook J., Fritsch E. F., and Maniatis T. 1989. "Molecular Cloning—A Laboratory Manual". Cold Spring Harbor Laboratory Press.
4. Fisher K J, Kelley W M, Burda J F, and Wilson J M. 1996. A novel adenovirus-adeno-associated virus hybrid vector that displays efficient rescue and delivery of the AAV genome. Hum. Gene Ther. 7(17):2079–2087.
5. Ausubel F M et al. 1994. Current Protocols In Molecular Biology. John Wiley & Sons, Inc.
6. Hirt B. 1967. Selective extraction of polyoma DNA from infected mouse cell cultures. J Mol Biol. 26(2):365–369.
7. Gao G P, Qu G, Faust L Z, Engdahl R K, Xiao W, Hughes J V, Zoltick P W, and Wilson J M. 1998. High-titer adeno-associated viral vectors from a Rep/Cap cell line and hybrid shuttle virus. Hum. Gene Ther. 9:2254–2362.
8. Xiao X, Li J, and Samulski R J. 1998. Production of high-titer recombinant adeno-associated virus vectors in the absence of helper adenovirus. J Virol. 1998. 72(3): 2224–2232.
9. Li J, Samulski R J, and Xiao X. 1997. Role for highly regulated rep gene expression in adeno-associated virus vector production. J Virol. 71(7):5236–5243.
10. Weitzman M D, Fisher K J, and Wilson J M. 1996. Recruitment of wild-type and recombinant adeno-associated virus into adenovirus replication centers. J. Virol. 70(3):1845–1854.
11. Gao G P, Yang Y, and Wilson J M. 1996. Biology of adenovirus vectors with E1 and E4 deletions for liver-directed gene therapy. J Virol. 70(12):8934–43.
12. Hardy S, Kitamura M, Harris-Stansil T, Dai Y, and Phipps L. 1997. Construction of Adenovirus Vectors through Cre-lox Recombination. J. Virol. 71(3), 1842–1849.

The invention claimed is:

1. An adenovirus vector for the manufacture of rAAV, wherein the adenovirus vector comprises an AAV rep gene, and wherein the AAV p5 promoter is deleted upstream of the AAV rep gene and said vector contains a minimal promoter in place of the p5 promoter, wherein the minimal promoter contains a TATA box as its only regulatory element.

2. An adenovirus vector for the manufacture of rAAV, wherein the adenovirus vector comprises an AAV rep gene, and wherein the AAV p5 promoter is deleted upstream of the AAV rep gene and said vector contains a minimal *Drosophila* heat shock promoter in place of the p5 promoter.

3. An adenovirus vector for the manufacture of rAAV, wherein the adenovirus vector comprises an AAV rep gene, and wherein the AAV p5 promoter is deleted upstream of the AAV rep gene and said vector contains a minimal adenoviral E1b promoter in place of the p5 promoter.

4. The adenovirus vector of claim 1, 2, or 3, wherein the adenovirus vector further comprises an AAV cap gene.

5. The adenovirus vector of claim 4, wherein the rep gene and the cap gene are inserted in place of at least a portion of one or more of the E1, E3 or E4 genes of adenovirus in a locus of the adenovirus vector.

6. The adenovirus vector of claim 5, wherein both the rep gene and the cap gene are inserted within the same locus of the adenovirus vector.

7. The adenovirus vector of claim 5, wherein the rep gene and the cap gene are inserted within different loci of the adenovirus vector.

8. The adenovirus vector of claim 4, wherein the rep and cap genes are from different AAV serotypes.

9. The adenovirus vector of claim 4, wherein the rep and cap genes are from the same AAV serotype.

10. A method for producing rAAV, comprising the steps of:
   a) infecting a host cell comprising a rAAV genome with the adenovirus according to claim 1, 2 or 3 wherein the infected host cell comprises helper functions and Cap coding sequences;
   b) growing the host cells under conditions in which rAAV is produced; and
   c) optionally collecting the rAAV from the host cells.

11. The method according to claim 10, wherein the rAAV genome is stably integrated in a chromosome of the host cells.

12. The method according to claim 10, wherein the host cell comprises an adenovirus vector comprising the rAAV genome and said host cell is co-infected with the adenovirus vector comprising the rep gene.

13. The method according to claim 10, wherein the adenovirus vector provides a helper function for rAAV production.

14. The method according to claim 13, wherein said helper function is provided by at least one gene product selected from the group consisting of adenoviral genes E1A, E1B, E2A, E4orf6 and VAI, or at least one gene product selected from the group consisting of HSV type 1 genes UL5, UL8, UL52, and UL29.

15. The method according to claim 10, wherein the host cell is a 293 cell.

16. The method according to claim 10, further comprising the step of purifying the rAAV.

17. The method according to claim 10, wherein the host cells are selected from CHO, BHK, MDCK, 10T1/2, WEHI cells, COS, BSC 1, BSC 40, BMT 10, VERO, WI38, MRC5, A549, HT1080, 293, B-50, 3T3, NIH3T3, HepG2, Saos-2, Huh7, HER, HEK, HEL, or HeLa cells.

18. A method for producing rAAV, comprising the steps of, growing a host cell comprising a rAAV genome and an adenovirus according to claim 1, 2 or 3 under conditions in which rAAV is produced and wherein the host cell further comprises helper functions and Cap coding sequences; and optionally collecting the rAAV from the host cells.

19. The adenovirus vector of claim 1, 2, or 3 wherein Rep78 and Rep68 are produced at lower levels than Rep52 and Rep40 in a cell into which the adenovirus vector has been introduced.

* * * * *